United States Patent [19]
Schoendorfer et al.

[11] Patent Number: 5,899,856
[45] Date of Patent: May 4, 1999

[54] DERMAL PATCH DETECTING LONG-TERM ALCOHOL CONSUMPTION AND METHOD OF USE

[75] Inventors: Donald W. Schoendorfer; William R. Miller, both of Santa Ana, Calif.

[73] Assignee: Sudormed, Inc., Santa Ana, Calif.

[21] Appl. No.: 08/747,304

[22] Filed: Nov. 12, 1996

Related U.S. Application Data

[63] Continuation-in-part of application No. 08/463,630, Jun. 6, 1995, abandoned, which is a continuation of application No. 07/989,204, Dec. 11, 1992, Pat. No. 5,441,048, which is a continuation-in-part of application No. 07/569,007, Aug. 15, 1990, Pat. No. 5,203,327, which is a continuation-in-part of application No. 07/241,707, Sep. 8, 1988, Pat. No. 4,957,108

[60] Provisional application No. 60/012,460, Feb. 28, 1996.

[51] Int. Cl.[6] .................................................. A61B 5/00
[52] U.S. Cl. ...................... 600/362; 600/573; 600/575; 604/312
[58] Field of Search ................................... 600/362, 363, 600/304, 366, 346, 573, 575, 584; 604/312

[56] References Cited

U.S. PATENT DOCUMENTS

| | | | |
|---|---|---|---|
| 4,329,999 | 5/1982 | Philips | 128/760 |
| 4,444,193 | 4/1984 | Fogt et al. | 128/632 |
| 4,732,153 | 3/1988 | Phillips | 128/636 |
| 4,756,314 | 7/1988 | Eckenhoff et al. | 128/760 |
| 4,909,256 | 3/1990 | Peck | 128/632 |
| 4,957,108 | 9/1990 | Schoendorfer et al. | 128/632 |
| 4,960,467 | 10/1990 | Peck | 106/209 |
| 5,050,604 | 9/1991 | Reshef et al. | 600/346 |
| 5,076,273 | 12/1991 | Schoendorfer et al. | 128/632 |
| 5,203,327 | 4/1993 | Schoendorfer et al. | 128/632 |
| 5,396,901 | 3/1995 | Phillips | 128/771 |
| 5,438,984 | 8/1995 | Schoendorfer | 128/632 |
| 5,441,048 | 8/1995 | Schoendorfer | 128/632 |
| 5,445,147 | 8/1995 | Schoendorfer et al. | 128/632 |
| 5,465,713 | 11/1995 | Schoendorfer | 128/632 |

FOREIGN PATENT DOCUMENTS

| | | | |
|---|---|---|---|
| 0099748 | 2/1984 | European Pat. Off. | A61F 13/02 |
| 0217403 | 4/1987 | European Pat. Off. | G01N 33/52 |
| 2157955 | 11/1985 | United Kingdom | A61F 13/02 |

OTHER PUBLICATIONS

Aly et al. (1978) Effect of Prolonged Occlusion on the Microbial Flora, pH, Carbon Dioxide . . . , *J. Invest. Dermatol.*, 71(6) :378–381.

Aly et al. (1988) Restriction of bacterial growth under commerical catheter dressings, *Am . J. Infect. Control*, 16(3):95–100.

Brown, D.J., (1985) The Pharmacokinetics of Alcohol Excretion in Human Perspiration, *Meth. Find. Exptl. Clin. Pharmacol.*, 7(10) :539–544.

Dover et al., (1995) Toxicity testing of wound dressing materials in vitro, *Brit. J. Plastic Surgery*, 48:230–235.

Jones, A.W., (1978) Variability of the Blood:Breath Alcohol Ration in Vivo, *J. Studies on Alcohol*, 39(11) :1931–1939.

Nyman, E. & Palmlov, A., (1936) The Elimination of Ethyl Alcohol in Sweat, *Scand. Arch. Physiol.* 74:155–159.

Peck et al., (1981) Continuous Transepidermal Drug Collection: Basis for Use in Assessing Drug . . . , *J. Pharmacokinetics and Biopharm.*, 9(1) :41–48.

(List continued on next page.)

*Primary Examiner*—Kenneth E. Peterson
*Assistant Examiner*—David M. Ruddy
*Attorney, Agent, or Firm*—Knobbe, Martens, Olson & Bear, LLP

[57] ABSTRACT

A non-occlusive dermal patch for collecting vapor phase perspiration from a subject's skin and retaining an analyte such as ethanol in the perspiration is disclosed. A method of collecting vapor phase perspiration containing an analyte such as ethanol over a period up to several days and detecting the analyte to determine the wearer's consumption of the analyte during the period when the patch was worn is disclosed.

40 Claims, 6 Drawing Sheets

OTHER PUBLICATIONS

Phillips et al., (1977) Long–Term Sweat Collection Using Salt–Impregnated Pads, *J. Invest. Derm.*, 68(4) :221–224.

Phillips et al., (1980) A Sweat–Patch Test for Alcohol Consumption: Evaluation . . . , *Alcoholism: Clin. Exp. Res.*, 4(4) :391–395.

Phillips et al., (1988) Evaluation of the Alcopatch, A Transdermal Dosimeter . . . , *Alcoholism: Clin. Exp. Res.*, 19(5).

Phillips, M., *The Alcopatch, Memo from Menssana, Inc.*, (Fort Lee, NJ 07074), 1 page.

Smith et al., (1986) Detection of Cocaine Metabolite in Perspiration Stain, Menstrual Bloodstain, and Hair, *J. Forensic Sci.*, 31(4) :1269–1273.

Spiehler, V.R. et al., (1988) Confirmation and Certainty in Toxicology Screening, *Clin. Chem.*, 34(8) :1535–1539.

Swift, R.M. et al., (1992) Studies on a Wearable, Electronic, Transdermal Alcohol Sensor, *Alcoholism: Clin. Exp. Res.*, 16(4) :721–725.

Swift, R.M., (1993) Transdermal measurement of alcohol consumption, *Addiction*, 88:1037–1039.

DERMAL PATCH DETECTING LONG-TERM ALCOHOL CONSUMPTION AND METHOD OF USE

RELATED APPLICATION

This application is a continuation-in-part of application Ser. No. 08/463,630, filed Jun. 6, 1995 now abandoned, which was a continuation of Ser. No. 07/989,204, filed Dec. 11, 1992, now U.S. Pat. No. 5,441,048, which was a continuation-in-part of Ser. No. 07/569,007, filed Aug. 15, 1990, now U.S. Pat. No. 5,203,327, which was a continuation-in-part of Ser. No. 07/241,707, filed Sep. 8, 1988, now U.S. Pat. No. 4,957,108, and claims priority to provisional application Ser. No. 60/012,460, filed Feb. 28, 1996, under 35 U.S.C. § 119(e).

FIELD OF THE INVENTION

The present invention relates to detecting an analyte in perspiration, and particularly relates to a dermal patch for collecting and retaining volatile ethanol in perspiration for analysis and detection of alcohol consumption over a period of hours to several days.

BACKGROUND OF THE INVENTION

Ethanol in alcoholic beverages is consumed regularly by about half of all adults and is the most frequently abused drug worldwide. Alcohol abuse results in substantial morbidity and mortality with the associated costs of medical care, accidents and lost productivity. State laws restrict driving under the influence of alcohol and many employees in safety-sensitive jobs, including school bus drivers, mass transit operators and commercial drivers, are prohibited from performing their jobs with blood alcohol levels above 0.04 g % or within four hours of consuming alcohol.

Ethanol distributes evenly throughout body fluids with the ethanol concentration proportional to the body fluid's water content. A single ethanol dose (1 g/kg body weight) raises the blood-alcohol level from the normal endogenous ethanol concentration of about 0.00015 g/dl to about 0.1 g/dl in about an hour on an empty stomach (Baselt, R. & Cravey, R., *Deposition of Drugs and Chemicals in Man*, 4th ed., p. 293, Chemical Toxicol. Inst., 1994). During the post-absorption phase, the ratio of ethanol in urine compared to whole blood averages 1.3, whereas the breath to whole blood ratio averages about 2180 and is related to the partition coefficient between blood alcohol in the lungs and alcohol vapor in air (Payne, J. P. et al., *Nature* 217:963, 1968; Heise, A. H., *J. For. Sci.* 12:454, 1967; Jones, A. W., *J. Stud. Alc.* 39:1931, 1978).

Alcohol in body fluids is commonly measured in a laboratory or in the field using enzyme assays, immunoassays, gas chromatography (GC), chemical oxidation and photometry, electrochemical oxidation with fuel cells, infrared spectrometry or solid-state semiconductor sensing. Breath and saliva ethanol measurements are commonly used for non-invasive instantaneous analysis and monitoring of alcohol use (Jones, A. W., *J. Ann. Tox.* 19:169, 1995). These methods provide an instant measurement of body fluid ethanol at the sampling time and are useful for determining the subject's condition at the specimen collection time, but provide no information on the subject's long-term or cumulative alcohol consumption. This is because the ethanol half-life in the body is relatively short, averaging 8 hr in breath, blood and urine (Baselt, R. & Cravey, R., *Deposition of Drugs and Chemicals in Man*, 4th ed., Chemical Toxicol. Inst., 1994). Thus, instantaneous measurements provide no information on alcohol use unless the sample is collected shortly after consumption.

Individuals who abuse alcohol often underreport the amount they consume. Moreover, blood carbohydrate-deficient transferins (CDT) that correlate with chronic alcohol abuse are only detected after relatively extreme levels of ethanol consumption (Bean, P. et al., *Clin. Chem.* 41(6):858, 1994). Thus, methods for monitoring long-term abstinence or limited alcohol consumption are needed for monitoring compliance with forensic and/or treatment programs.

Biological analytes can exit the body in either insensible or sensible perspiration. Insensible perspiration results from passive diffusion of water and other volatiles through the skin. Insensible perspiration varies with location on the body and skin temperature but is relatively similar on the upper arms, back, and lower chest. In contrast, sensible perspiration is actively secreted from eccrine and apocrine sweat glands (located, respectively, throughout the skin and in the axilla, pubic and mammary areas).

Many drugs, including ethanol, are excreted in sweat (Nyman, E. & Palmlov, A., *Scand. Arch. Physiol.* 74:155, 1936). During absorption, alcohol concentration of insensible sweat lags behind that of blood and breath but after complete absorption, the ethanol concentrations in insensible perspiration, breath and blood are similar. At the beginning of the post-absorption phase, when blood and breath levels begin to drop, the alcohol concentration of insensible sweat is slightly higher. During post-absorption, the alcohol elimination rate constant from skin is similar to that of blood and breath (Brown, D., *Meth. Find. Exptl. Clin. Pharmacol.* 7(5):269, 1985; Brown, D., *Meth. Find. Exptl. Clin. Pharmacol.* 7(10):539, 1985).

Because perspiration can be collected noninvasively, it is preferable to blood collection, an invasive procedure, or urine collection which involves privacy concerns and samples that can be readily adulterated. Collecting perspiration samples for analyte analysis is known. For example, clothing worn by an individual can be extracted and analyzed for drugs (Smith et al., *J. Forensic Sci.* 36:582–585, 1981; *J Forensic Sci.* 31:1269–1273, 1986). Perspiration induced by exercise, thermal stress or pilocarpine iontophoresis (a procedure involving small amounts of electrical current) can be collected and analyzed. A sensor placed on the skin and attached to a battery-operated device can electrochemically measure and record the skin ethanol vapor concentration every two to five minutes (Swift, R. M., et al., *Alcoholism: Clin. Exp. Res.* 16(4):721, 1992).

Occlusive dermal patches for collecting and retaining perspiration and analytes therein have been used to monitor exposure to chemicals including alcohol as described in U.S. Pat. No. 4,329,999, U.S. Pat. No. 4,732,153 and U.S. Pat. No. 5,396,901. These occlusive transdermal dosimeters utilize a waterproof dermal adhesive patch for collecting, storing and processing perspiration.

Occlusive dermal patches to collect perspiration generally have significant disadvantages. Hydration alters the skin's steady-state pH, affects transepidermal water loss and carbon dioxide emission rates, promotes growth of microbial species that colonize the skin and results in skin irritation. After three to five days, the pH of skin, the transepidermal water loss and carbon dioxide emission rates, and the number of microbes under an occlusive patch all increased significantly (Aly, Raza et al., *J Invest. Dermatol.* 71(6):378–381, 1978; Aly, Raza, et al., *Am. J Infec. Control* 16(3):95–100, 1988). In some cases, antifungal and antimicrobial agents have been included in occlusive patches to inhibit microbial growth and glycolysis by microbes growing in or under the patch (U.S. Pat. No. 4,329,999 and U.S. Pat. No. 4,732,153). Perspiration also tends to leak from some occlusive patches affecting analyte analysis results.

Carbon (e.g., activated charcoal) has been used to selectively adsorb volatile solutes in gas or liquid that contacts the carbon particles. Charcoal is activated by exposing it to high temperatures in a controlled atmosphere to produce microscopic pores in the carbon crystalline lattice. These pores are responsible for adsorption of compounds.

Some dermal patches have included activated charcoal as a binding material. For example, U.S. Pat. No. 4,732,153 discloses a transdermal dossier to monitor exposure to chemical agents by providing an unbroken fluid link between tissue fluids in the skin and the fluid collecting component which may include activated charcoal as a binding material. Similarly, U.S. Pat. No. 5,396,901 describes a watertight transdermal dossier connected by a fluid bridge to the skin for storing collected fluid and chemical substances in a tamper-resistant container. U.S. Pat. No. 4,756,314 describes an osmotically-driven absorbent sweat collection pad, which may contain activated charcoal, in a patch that stores fluid phase water and substances in perspiration for determining the presence of low molecular weight substances in sweat. U.S. Pat. No. 4,909,256 discloses a transdermal patch that includes a charcoal-containing binding reservoir in an airtight adhesive cover for monitoring exposure to chemical substances including ethanol. U.S. Pat. No. 4,960,467 describes an occlusive patch for collection of liquid transdermal substances in a wettable substance binding reservoir of activated charcoal powder immobilized in a gel matrix.

Carbon-containing wound dressings are also known. These include KALTOCARB™ (Britcair), made of alginate and charcoal; OPRASORB™ (Lohmann GmbH & Co. KG, Nuweid, Germany), an activated charcoal cloth; and LYOFOAM™ (Seton Healthcare), a charcoal-containing polyurethane foam (Dover et al., *Brit. J Plastic Surgery* 48:230235, 1995; Wollina et al., *Skin Pharmocol.* 9:35–42, 1996).

Dermal patches that collect components of perspiration have been described in U.S. Pat. No. 5,203,327 and U.S. Pat. No. 4,957,108, both hereby incorporated by reference.

The non-occlusive dermal patch of the present invention overcomes many of the disadvantages associated with other transdermal patches and methods of monitoring alcohol consumption. This dermal patch collects and retains volatile alcohol in vapor phase perspiration during the entire period the patch is worn, thus providing a system of monitoring ethanol consumption for over a week without collecting and storing liquid perspiration or causing skin irritation.

SUMMARY OF THE INVENTION

According to the invention, there is provided a dermal patch for determining the presence of an analyte in perspiration of a subject mammal. The dermal patch includes an adsorbent material for collecting perspiration in vapor phase from the subject's skin and retaining a vapor phase analyte present in the collected vapor phase perspiration, the adsorbent material having a first side and a second side and an outer perimeter, wherein the first side is adapted to be in fluid communication with the subject's skin; a first gas permeable film having a first side and a second side and an outer perimeter, wherein the first side of the gas permeable film is adjacent to the second side of the adsorbent material and wherein the first gas permeable film has a first moisture vapor transmission rate (MVTR) whereby perspiration expressed through the subject's skin is permitted to escape in vapor phase from the patch through the first gas permeable film; and a second gas permeable film having a first side and a second side and an outer perimeter, wherein the first side of the second gas permeable film is adapted to be in fluid communication with the subject's skin and the second side of the second gas permeable film is located adjacent to the first side of the adsorbent material, and wherein the second gas permeable film has a second MVTR that is no more than about equal to the first MVTR. One embodiment further includes an adhesive layer on the first side of the first gas permeable film, the adhesive layer for attaching the patch to the subject's skin. Another embodiment further includes an adhesive layer on the first side of the second gas permeable film, the adhesive layer for attaching the patch to the subject's skin. One embodiment also includes a release liner having a first side and a second side, wherein the release liner is located between the first gas permeable film and the adsorbent material such that the first side of the release liner is adjacent to the first side of the first gas permeable film and the second side of the release liner is adjacent to the second side of the adsorbent material. Another embodiment further includes an outer protective liner located proximate to the second side of the first gas permeable film, to the first side of the second gas permeable film, or both. In one embodiment, the adsorbent material includes activated carbon in an inert matrix. In another embodiment, the analyte retained in the adsorbent material includes ethanol. In a preferred embodiment, the first or second gas permeable film comprises polyurethane. The dermal patch of another embodiment further includes a pouch for containing the dermal patch before use, after use or both. Another embodiment also includes indicia incorporated into the dermal patch for identifying the dermal patch.

According to another aspect of the invention, there is provided a dermal patch to be worn on the skin of a subject mammal for determining the presence of ethanol in the subject's perspiration, including a carbon-containing adsorption pad for collecting vapor phase perspiration from a subject's skin and retaining vapor phase ethanol present in the collected perspiration, the adsorption pad having a first side and a second side, wherein the first side is adapted to be in fluid communication with the subject's skin; a first gas permeable film having a first side and a second side and an outer perimeter, wherein the first side of the gas permeable film is located adjacent to the second side of the carbon-containing adsorption pad, and wherein the first gas permeable film has a first moisture vapor transmission rate (MVTR); and a second gas permeable film having a first side and a second side and an outer perimeter, wherein the first side of the second gas permeable film is adapted to be in fluid communication with the subject's skin and the second side of the second gas permeable film is located adjacent to the first side of the adsorption pad, and wherein the second gas permeable film has a second MVTR that is no more than about equal to the first MVTR. One embodiment further includes an adhesive layer on the first side of the gas permeable film, the adhesive layer for attaching the patch to the subject's skin. Another embodiment further includes an adhesive layer on the first side of the second gas permeable film, the adhesive layer for attaching the patch to the subject's skin. In one embodiment, the first or second gas permeable film includes polyurethane. In another embodiment, the first and second gas permeable films include polyurethane. One embodiment also includes a release liner having a first side and a second side, wherein the release liner is located between the first gas permeable film and the adsorption pad such that the first side of the release liner is adjacent to the first side of the first gas permeable film and the second side of the release liner is adjacent to the second side of the adsorption pad. In a preferred embodiment, the adsorption pad includes activated charcoal in an inert matrix. Another embodiment further includes a pouch for containing the dermal patch before use, after use or both. A preferred embodiment also includes indicia for identifying the dermal patch.

According to another aspect of the invention, there is provided a dermal patch for determining the presence of an analyte in perspiration of a subject mammal, including a first adsorption pad for collecting perspiration in vapor phase from the subject's skin and retaining a vapor phase analyte present in the vapor phase perspiration, the adsorption pad having a first side and a second side and an outer perimeter, wherein the first side is adapted to be in fluid communication with the subject's skin; a second adsorption pad for collecting the vapor phase analyte from the subject's environment and retaining the analyte, the second adsorption pad having a first side and a second side and an outer perimeter, wherein the second side is adapted to be in fluid communication with the subject's environment; a first gas permeable film having a first side and a second side and an outer perimeter, wherein the first side of the gas permeable film is adjacent to a second side of at least one adsorption pad, wherein the second side of the gas permeable film is adapted to be in fluid communication with the subject's environment, and wherein perspiration expressed through the subject's skin is permitted to escape in vapor phase from the patch through the first gas permeable film; a second gas permeable film having a first side and a second side and an outer perimeter, wherein the first side of the second gas permeable film is adapted to be in fluid communication with the subject's skin, wherein the second side of the second gas permeable film is located adjacent to a first side of at least one adsorption pad, and wherein the first side of the gas permeable film is adapted to be in fluid communication with the subject's skin; and a separator layer located between the first adsorption pad and the second adsorption pad. In one embodiment, the separator layer has a first side and a second side, and the first side of the separator layer is located proximate to the second side of the first adsorption pad and the second side of the separator layer is located proximate to the first side of the second adsorption pad. In another embodiment, the first adsorption pad is located proximate to the second adsorption pad in a side-by-side arrangement such that a portion of the perimeter of the first adsorption pad is proximate to a portion of the perimeter of the second adsorption pad and the separator layer is located adjacent to the perimeter and the first side of the second adsorption pad, thereby separating the proximate portions of the perimeters of the first and second adsorption pads and separating the second adsorption pad from the second gas permeable film. One embodiment also includes an outer protective liner located adjacent to the first side of the second gas permeable film. Another embodiment includes an outer protective liner located adjacent to the second side of the first gas permeable film. In one embodiment, the analyte includes ethanol. One embodiment also includes a pouch for containing the dermal patch before use, after use or both. Another embodiment also includes indicia incorporated into the dermal patch for identifying the dermal patch.

According to another aspect of the invention, there is provided a method of determining the presence of an analyte contained in the perspiration of a subject mammal, comprising the steps of removably attaching a dermal patch to a subject's skin, wherein the dermal patch comprises a carbon-containing material capable of adsorbing a vapor phase analyte contained in the subject's perspiration, a first gas permeable film and a second gas permeable film, wherein the carbon-containing material is located between the first and second gas permeable films and is adapted to be in fluid communication with the subject's skin when the dermal patch is placed on the subject's skin, and wherein the first gas permeable film permits vapor phase perspiration to escape from the dermal patch; passing vapor phase perspiration containing the analyte expressed from the subject's skin through the carbon-containing material for a period of time sufficient to adsorb the analyte; removing the dermal patch after a period of time sufficient to adsorb the analyte has elapsed; and determining the amount of analyte adsorbed in the carbon-containing material. In one embodiment, the removing step occurs about one hour to about ten days after the attaching step. In another embodiment, the determining step includes extracting the analyte from the carbon-containing material to produce an extract. In another embodiment, the analyte comprises ethanol which is extracted from the carbon-containing material with water. In a preferred embodiment, the method further includes a step of measuring the analyte in the extract by gas chromatography. In one embodiment, the method includes a step of examining the dermal patch for evidence of tampering or of partial or complete removal of the dermal patch before the removing step. In one embodiment, the attaching step includes attaching a dermal patch to skin on the subject's arm, the back, the chest or any combination thereof. In one embodiment, the analyte includes ethanol. In another embodiment, the dermal patch further includes a second carbon-containing material that is adapted to be in fluid communication with the vapor phase analyte in the subject's environment, and the method further includes the steps of collecting the vapor phase analyte in the subject's environment during the period when vapor phase perspiration containing the analyte is passed through the carbon-containing material and determining the amount of the analyte adsorbed in the second carbon-containing material. Another embodiment includes the step of comparing the amount of analyte in the second carbon-containing material with the amount of analyte in the carbon-containing material through which vapor phase perspiration passed to determine an amount of the analyte in the subject's perspiration during the period when vapor phase perspiration containing the analyte passed through the carbon-containing material.

According to another aspect of the invention, there is provided a method of indicating alcohol consumption by a patient. This method includes the steps of identifying a patient to be monitored for alcohol consumption, providing a non-occlusive dermal patch having an activated charcoal layer therein, securing the dermal patch to the skin of the patient for a period in excess of about one day, permitting moisture in perspiration to escape from the patient and through the dermal patch during the period in which the patch is secured to the patient's skin, removing the dermal patch from the skin of the patient, and measuring ethanol or a metabolite of ethanol contained in the activated charcoal layer. In one embodiment of this method, the period in which the patch is secured to the patient's skin is up to about ten days. In another embodiment, the metabolite of ethanol that is measured is acetaldehyde.

DETAILED DESCRIPTION OF THE PREFERRED EMBODIMENT

The dermal patch of the present invention includes a carbon-containing adsorbent material to collect analytes including ethanol excreted in perspiration, where the water and substances contained in perspiration enter the adsorbent material in vapor rather than liquid form. For perspiration collection, the non-occlusive dermal patch is attached to the skin of the user with an adhesive material. The adsorbent material is preferably activated carbon that is kept dry by a non-occlusive film separating the adsorbent material from liquid perspiration present on the skin and another non-occlusive film to prevent exposure of the adsorbent material to liquid in the environment while allowing vapor phase perspiration to exit the patch. Thus, the gas permeable dermal patch allows volatilized perspiration substances to enter the patch where the adsorbent material collects and holds analytes including ethanol while allowing vapor phase water to escape from the patch. Gas permeability allows the patch to be worn for relatively long periods of time (many days) to collect volatilized substances in the adsorbent material without becoming saturated with liquid perspiration and uncomfortable to the wearer. Because volatilized ethanol present in perspiration can be collected and held in the dermal patch over the course of many days, the patch is useful for detecting ethanol consumption by the patch wearer during the entire wearing period and provides a means of measuring total ethanol consumption during the wearing period. The collected ethanol may be detected and measured by chemical, electrochemical, immunochemical or chromatographic methods well known in the art.

The term "non-occlusive" is used herein to describe a material that will permit the passage of vapor phase water and other volatilized small molecules in perspiration such as volatile ethanol but will exclude liquid phase water and other larger molecules. In contrast, "occlusive" refers to materials that are substantially vapor impermeable and liquid impermeable. The term "gas permeable" is used to describe material that permits the passage of gases, including the vapor phase of fluids expressed from the skin.

Figure 1:
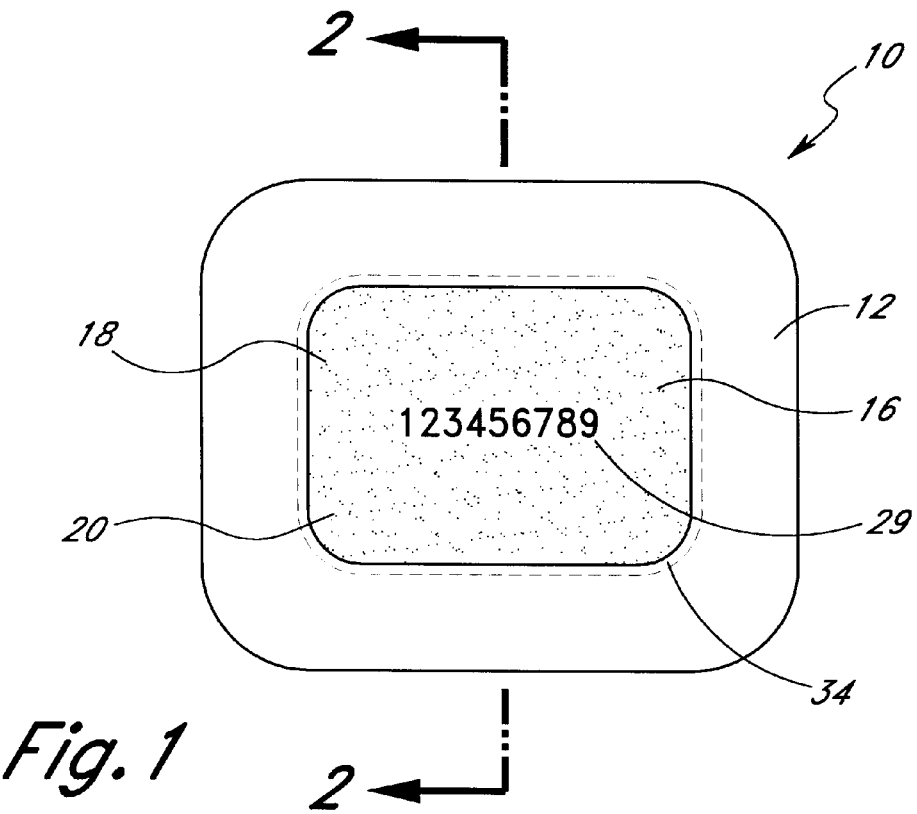
FIG. 1 is a plan view of a dermal patch with a single adsorption pad for ethanol collection from perspiration.
Figure 2:
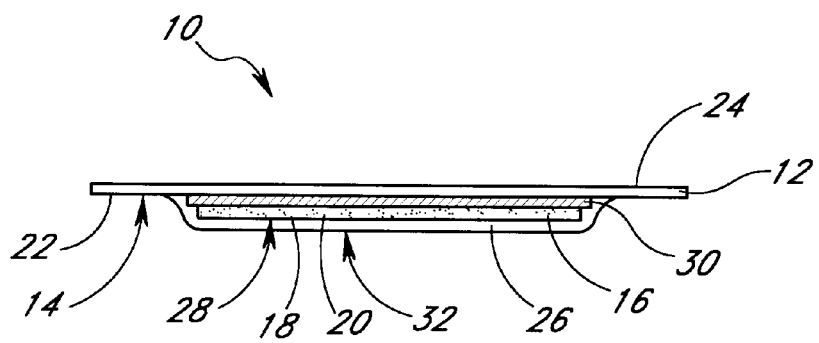
FIG. 2 is a cross-sectional view of the dermal patch taken along the line 2—2 of FIG. 1.

Referring to FIGS. 1 and 2, one embodiment of the dermal patch 10 includes a first non-occlusive film 12 with an attached adhesive layer 14 and an adsorption pad 16 made of an adsorbent material that is a porous layer of activated carbon 18 (i.e., activated charcoal) immobilized in an inert matrix 20, such as nylon, polyester, polyurethane, polytetrafluoroethylene (PTFE), polystyrene and other known polymers. Preferably the first non-occlusive film 12 is a very thin polyurethane (e.g., about 0.001 inch) film with an acrylate adhesive applied to a first lower surface 22 of the film 12. The non-occlusive film 12, when applied to the skin using the adhesive 14 covers the skin but allows water content of perspiration to evaporate, exiting from a second upper surface 24 of the film. A preferred non-occlusive film is a hypoallergenic, water-resistant polyurethane film with an adhesive layer (e.g., as used in TEGADERM-1625® dressing; 3M Health Care, St. Paul, Minn.). Preferably the non-occlusive film 12 is attached to the skin by the adhesive layer 14 for periods up to about eight to ten days without causing adverse dermatological reactions. The polyurethane film 12 is preferably 6 cm×7 cm and 0.025 mm thick.

The dermal patch 10 may be removably attached to the subject's skin using the adhesive layer 14 such that the adsorption pad 16 is located adjacent to the wearer's skin and is held in place by the first non-occlusive film 12. The dermal patch 10 also includes a second non-occlusive film 26 covering a lower surface 28 of the adsorption pad 16, such that the second non-occlusive film 26 separates the adsorption pad from the wearer's skin when the patch 10 is placed on the subject's skin and prevents liquid perspiration from contacting the activated carbon of the adsorption pad because liquid water in perspiration could potentially desorb ethanol retained in the pad. The second non-occlusive film 26 also prevents discoloration of the wearer's skin resulting from direct contact with the activated carbon 18 of the adsorption pad 16. Thus, the adsorption pad 16 is sandwiched between an upper first non-occlusive film 12 and a lower second non-occlusive film 26. When the patch is worn on a subject's skin, the first film is exposed to the environment and the second film is adjacent to the wearer's skin. Preferably, both films are of the same non-occlusive polyurethane material.

Preferably, the adsorption pad 16 is a rectangle (3.18 cm×4.76 cm×1.0 mm) with rounded corners made of activated carbon 18 immobilized in an expanded polytetrafluoroethylene (PTFE) matrix. The preferred adsorption pad 16 has an area of about 14 cm$^2$ and contains about 540 mg of activated carbon, with no other chemicals or substances needed to retain ethanol. A preferred material for the adsorption pad is DARCO G-60® medium (3M Health Care, St. Paul, Minn.).

The dermal patch 10 may include indicia 29 to identify the patch. For example, as shown in FIG. 1, a multi-digit serial number or bar code may be printed underneath the first film 12 so that the identification indicia can be read through the film when the dermal patch is applied to a wearer's skin. Alternatively, the indicia may be placed under the second film, to be visible before the patch is applied or after it is removed from the subject's skin. Such indicia are useful for chain-of-custody identification of the dermal patch.

Referring to FIG. 2, the dermal patch 10 may also include a release liner 30 to allow removal of the adsorption pad 16 from the adhesive layer 14 following dermal patch use. The release liner 30 shields the adsorption pad 16 from the adhesive layer 14 and prevents the adsorption pad from sticking to the adhesive. Preferably, the release liner 30 is a very thin (0.003 mm) medical grade cellulosic tissue (e.g., 1-ply 17# drape from James River Corporation, Gouverneur, N.Y.). The release liner 30 is preferably slightly larger than the adsorption pad 16 (about 3 cm×5 cm).

The lower adhesive side 32 of the second non-occlusive film 26 is proximate to the wearer's skin when the dermal patch 10 is adhered to a subject, thus adding to the total adhesive surface area of the patch. The second non-occlusive film 26 is adhered to the first non-occlusive film 12 having an adhesive layer 14 by adhesion between the two films in a portion of the border area 34 around the perimeter of the pad 16 or by any of a variety of other methods (e.g., spot welding). Preferably, the entire border area 34 around the perimeter of the adsorption pad is about 30 mm wide.

As shown in FIG. 2, the adsorption pad 16 is sandwiched between the two non-occlusive films 12, 26. The second non-occlusive film 26 protects the adsorption pad 16 from contact with liquid perspiration that may appear under the dermal patch 10 during use. The absolute humidity between the two non-occlusive films 12, 26 is controlled in a relatively narrow range by the moisture vapor transmission rates (MVTR) of the two films, defined as the amount of water vapor passing through a specified area of film in a specified time (e.g., $g/m^2/24$ hr) under specified conditions. This property improves the ability of the dermal patch 10 to retain captured ethanol in the adsorption pad 16. The MVTR of the first non-occlusive layer 12, the outer layer when the patch is worn, should be greater than or about equal to the MVTR of the inner second non-occlusive film 26 to keep the activated carbon of the adsorption pad 16 sufficiently dry to efficiently retain collected ethanol. If the MVTR of the outer first non-occlusive film is significantly less than the MVTR of the inner second non-occlusive film, the carbon of the adsorption pad may become saturated with perspiration water vapor which can condense to form liquid water that can desorb ethanol from the adsorption pad thus creating an inaccurate measurement of the collected perspiration ethanol. Thus, by choosing two non-occlusive films that have appropriate permeability characteristics, the dermal patch under normal usage conditions (i.e., substantially at body temperature) adsorbs vapor phase perspiration components that pass through the patch, releases nonadsorbed components from the patch in vapor phase at a rate sufficient to prevent condensation of perspiration within the patch, and prevents liquid components of perspiration or from the environment from contacting the adsorptive material within the patch. For example, a patch made of a material having an MVTR of about 450 to 850 $g/m^2/24$ hr, preferably 640 to 810 $g/m^2/24$ hr, is envisioned, where the MVTR of the first outer non-occlusive layer 12 layer is greater than or about equal to the MVTR of the inner second non-occlusive film.

Figure 3:
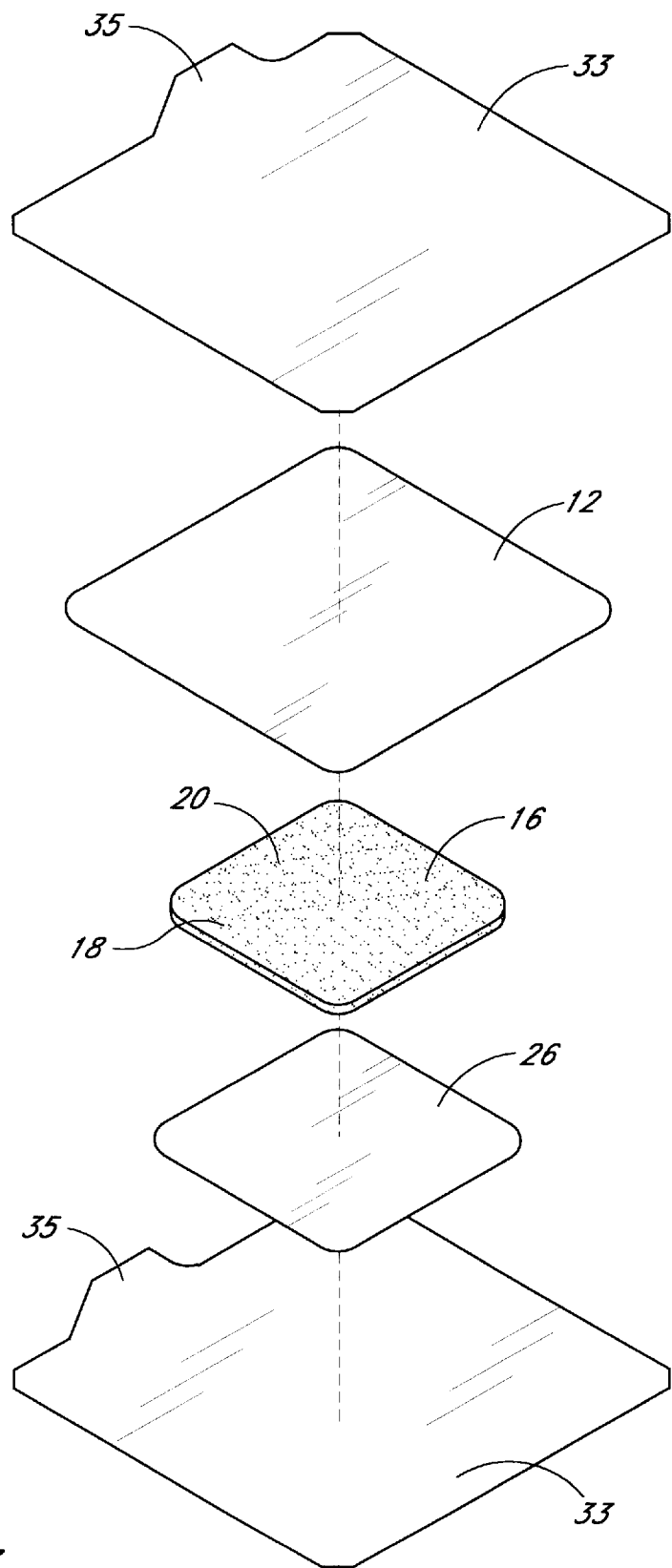
FIG. 3 is an exploded perspective view of the dermal patch including outer protective liners.

FIG. 3 illustrates an embodiment of the dermal patch in an exploded view showing the first non-occlusive film 12, the adsorption pad 16, the second non-occlusive film 26 and two outer protective liners 33. Outer protective liners 33 are protective barriers for use during storage and handling of the dermal patch. Preferably there are two outer protective liners 33, one liner covering each non-occlusive film 12, 26 of the dermal patch. The protective liners may be made of paper, woven or nonwoven fabric, plastic film or other similar materials. The protective liners are removed before dermal patch application. The outer protective liners may be attached to each other by an adhesive layer (e.g., around the perimeter of each liner) and may include tabs 35 for easily gripping the individual liners to aid in their removal.

Figure 4:
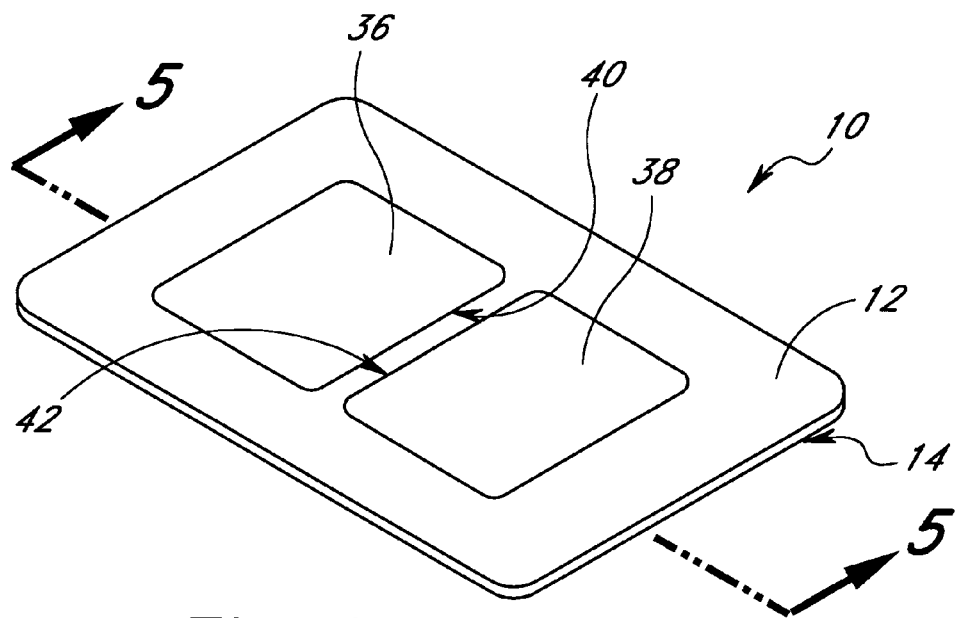
FIG. 4 is a perspective view of a dermal patch having two side-by-side adsorption pads, one for monitoring environmental exposure and one for collecting ethanol in perspiration.
Figure 5:
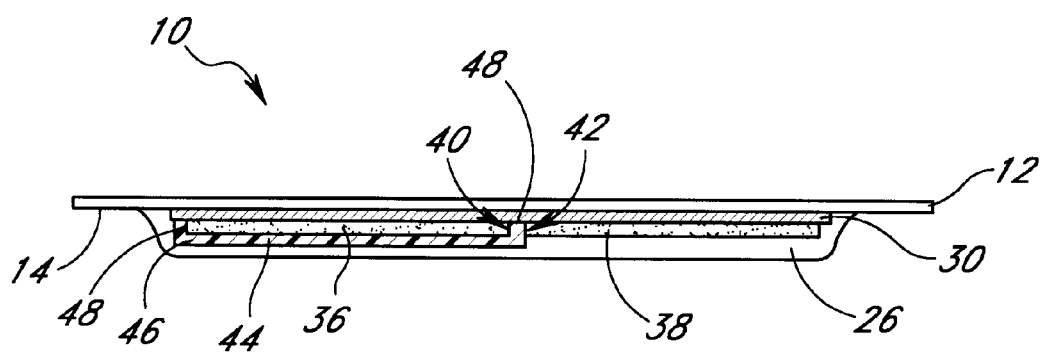
FIG. 5 is a cross-sectional view of a dermal patch taken along the line 5—5 of FIG. 4.

FIGS. 4 and 5 illustrate another embodiment of a dermal patch 10 with two adsorption pads arranged side-by-side in the patch. A first adsorption pad, the environmental indicator pad 36, monitors alcohol in the wearer's environment and serves as an internal measurement of potential contamination of the second pad, the collection pad 38, that collects the wearer's perspiration for measurement of the wearer's alcohol consumption. The two adsorption pads 36, 38 are both directly under the first non-occlusive film 12 with the adhesive layer 14 and arranged side-by-side so that a portion of the perimeter 40 of the environmental indicator pad 36 is proximate to a portion of the perimeter 42 of the collection pad 38. To avoid perspiration from entering the environmental indicator pad 36, a first separator layer 44 is located adjacent to the bottom surface 46 and second separator layer 48 is located substantially around the perimeter 40 of the environmental indicator pad 36 to effectively separate the pad 36 from the wearer's skin during use and prevent fluid communication of perspiration into the environmental indicator pad 36. The second separator layer 48 also prevents cross-contamination between the environmental indicator pad 36 and the collection pad 38 because it is located between the adjacent perimeter portions 40, 42 of the two pads. The first and second separator layers may be integral, formed from a single contiguous layer or may be separate but cooperating components with one component adjacent to the bottom surface 46 of the environmental indicator pad 36 and a second component essentially perpendicular to the first component and surrounding the perimeter 40 of the environmental indicator pad 36. Preferably the separator layers 44, 48 are made of an occlusive material that covers only the environmental indicator portion of the patch so that the patch 10 remains substantially non-occlusive and allows vapor phase perspiration to escape from the patch. The separator layers 44, 48 may be made of any of a variety of well known pliable occlusive materials such as films of metal foil or polymers such as polyvinylidene chloride, polyester, polyethylene terephthalate, polyvinyl fluoride or polyvinyl chloride, polyolefin, polyethylene, polypropylene, PTFE or nitrocellulose. Suitable occlusive materials have an MVTR that is about 0.01% to about 1% that of the nonocculsive film and are readily available (e.g., ALUREX CX®, St. Regis Paper Co. or SARAN®, Dow Chemical).

The patch 10 having both environmental indicator 36 and collection 38 pads is applied and worn as described for the single-pad patch. After the subject has worn the patch for the required testing period, the environmental indicator and collection pads are independently removed from the patch as described for the single-pad patch and analyzed independently for their ethanol content. Because both pads have been exposed to potential environmental contaminants, but only the collection pad has been exposed to the subject's perspiration, the ethanol concentration detected in the environmental indicator pad measures environmental contamination of the dermal patch and is a baseline measurement for ethanol detection by the collection pad. That is, the amount of ethanol detected in the environmental indicator pad is subtracted from that detected in the collection pad to determine the subject's ethanol consumption during the wearing period. If the collection pad contains significantly more ethanol than the environmental indicator pad, then the difference in the amounts of ethanol detected represents a measure of the subject's ethanol consumption during the wearing period. But if the amount of ethanol detected in the environmental indicator pad equals or exceeds the ethanol detected on the collection pad, then the subject's perspiration did not contain any detectable ethanol during the wearing period, meaning the subject did not consume ethanol then.

Figure 6:
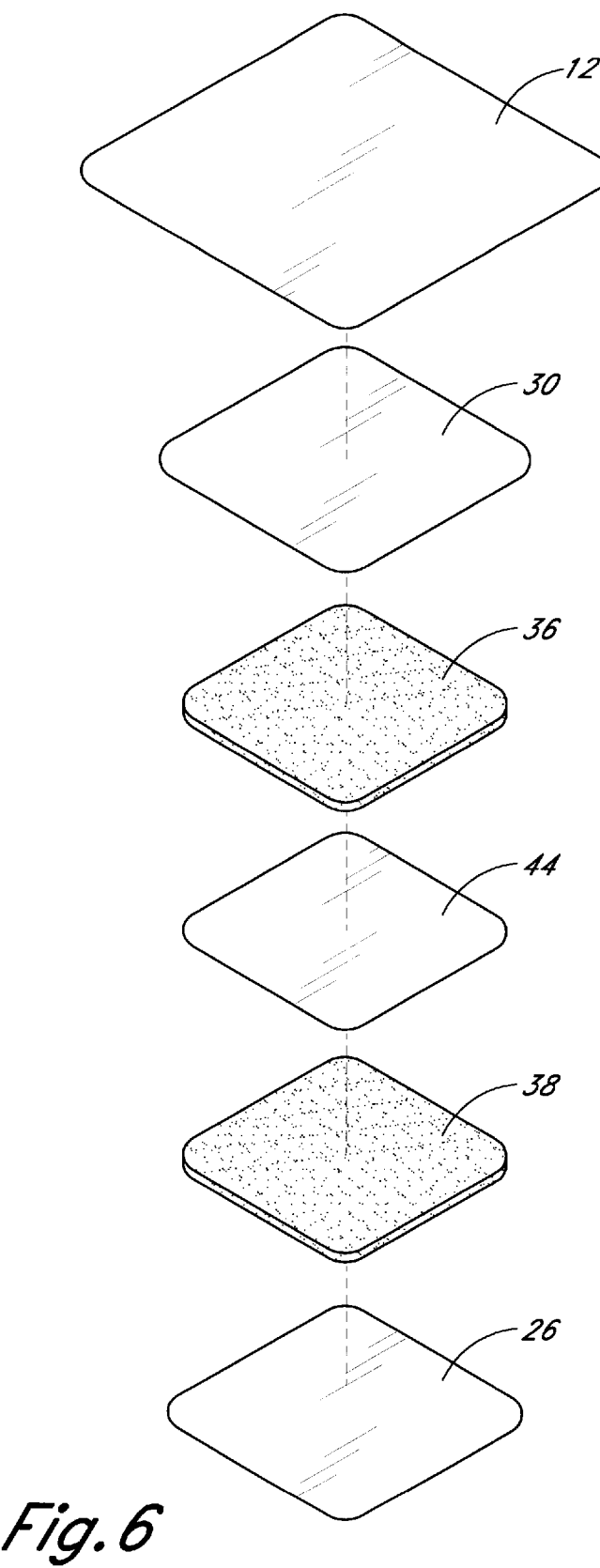
FIG. 6 is an exploded perspective view of a dermal patch having an upper adsorption pad for monitoring environmental exposure and a lower adsorption pad for collecting ethanol in perspiration.

FIG. 6 shows another embodiment of the dermal patch 10 having two adsorption pads, a first upper environmental indicator pad 36 and a second lower collection pad 38 with separator 44 between the two pads. "Upper" and "lower" refer to the relative positions of the two pads when the patch is attached to a subject's skin. The separator 44 between the upper and lower pads 36, 38 is preferably of the same non-occlusive polyurethane film as used in the first non-occlusive film 12. The environmental indicator pad 36 collects ethanol and other volatiles primarily from the external environment and serves as a standard for environmental contamination during the time the dermal patch 10 is worn. The collection pad 38 collects ethanol in perspiration and serves as a measure of alcohol consumption during the wearing period. Because of the efficiency of adsorption in the collection pad 38, ethanol in perspiration is retained in the collection pad 38 and does not substantially escape into the upper pad 36 despite the non-occlusive nature of the separator 44. Both the first and second adsorption pads 36, 38 are preferably made of highly porous layer of activated carbon 18 immobilized in an inert matrix 20, such as PTFE, nylon, polyester, polyurethane, polystyrene or other known polymers. The dermal patch includes a first non-occlusive film 12, preferably of very thin polyurethane with an attached acrylate adhesive layer 14 applied to a first lower surface 22 of the film 12. This embodiment also has a second lower non-occlusive film 26 with an adhesive lower surface 32 adjacent to the collection pad 38 such that the adhesive lower surface 32 contacts the wearer's skin when the patch is attached to a subject. The second lower non-occlusive film 26 is preferably of the same type of polyurethane as the first non-occlusive film 12. The second non-occlusive film 26 protects the collection pad 38 from liquid perspiration on the wearer's skin and its adhesive lower surface 32 provides additional adhesive surface for attachment of the dermal patch to the wearer's skin.

This embodiment includes a release liner 30 located between the environmental indicator pad 36 and the adjacent non-occlusive film 12 to prevent the pad from sticking to the adhesive layer 14 and aid in removal of the environmental indicator pad 36. Preferably, the release liner is made of thin (0.002 to 0.010 mm) medical grade cellulosic tissue and is slightly larger than the dimensions of the adjacent environmental indicator pad.

When the dual pad dermal patch shown in FIG. 6 is applied to a wearer's skin, vapor phase perspiration enters the patch through the second non-occlusive film 26 and encounters the collection pad 38 where volatile ethanol and other analytes are adsorbed by the activated charcoal. The water vapor and other volatile non-adsorbed substances then pass through the non-occlusive separator layer 44, the environmental indicator pad 36, the release liner 30, and the first non-occlusive film 12 to exit the patch to the environment. The environmental indicator pad 36 primarily encounters substances present in the wearer's environment outside of the patch which enter the patch through the first non-occlusive film and the release liner 30. Any ethanol from perspiration that is not adsorbed by the collection pad 38 may be adsorbed by the environmental indicator pad 36 as the volatile substances pass from the subject's skin through the patch. This would result in a somewhat higher baseline for ethanol detected in the environmental indicator pad.

For the patches with an environmental indicator pad 36 and a collection pad 38, such as illustrated in FIGS. 4–6, the ethanol detected in the environmental indicator pad is subtracted from that of the collection pad to determine if the subject has consumed ethanol during the testing period. That is, the amount of collection pad ethanol minus the amount of environmental pad ethanol correlates with the level of ethanol consumption. For example, if the subject consumes one dose of ethanol (equivalent to 1 g/kg) the level of ethanol detected in the collection pad is typically 50 nl. If the same subject was not exposed to significant levels of environmental alcohol, then the level detected in the environmental indicator pad is typically less than 10 nl and the difference of these two levels (50 nl–10 nl=40 nl) suggests that the subject consumed sufficient ethanol during the testing period to accumulate detectable ethanol (40 nl) in the dermal patch. If the subject is exposed to environmental ethanol and the level of ethanol detected in the environmental indicator patch substantially equals or exceeds that of the collection pad, it suggests that the subject has not consumed ethanol during the test period, although the subject may have been exposed to some environmental volatile ethanol such as present in cosmetics or household cleaners. For example, if the collection pad contains 15 nl of ethanol and the environmental indicator pad contains 14 nl of ethanol, then the difference is negligible (15 nl–14 nl=1 nl), suggesting the subject did not consume ethanol during the testing period. Similarly, a negative difference between the ethanol detected in the collection pad and the environmental indicator pad suggests that the subject did not consume ethanol during the testing period but was exposed to some environmental volatile ethanol. For example, if the collection pad contains 10 nl of ethanol and the environmental indicator pad contains 20 nl of ethanol, then the negative difference (10 nl–20 nl=–10 nl) suggests that the subject did not consume ethanol during the testing period. If the amount of ethanol in the environmental indicator pad (e.g., 1,000 nl) greatly exceeds that of the collection pad (50 nl) but the amount of ethanol in the collection would otherwise suggest consumption, then the difference (50 nl–1,000 nl=–950 nl) formally suggests that the subject did not consume ethanol during the testing period, but also suggests considerable exposure of the patch to environmental alcohol, possibly due to patch tampering.

The measurements made using by the dermal patch as illustrated in FIGS. 4 and 5, for the side-by-side collection and environmental indicator pads may differ somewhat from those made using the dermal patch as illustrated in FIG. 6, where the environmental indicator pad is located above the collection pad when the patch is worn by a subject. That is, the side-by-side arrangement allows use of an occlusive separator layer separating the environmental indicator pad from the skin and from the collection pad while maintaining the substantially nonocclusive nature of the dermal patch. In contrast, the embodiment shown in FIG. 6 is completely nonocclusive and relies on the collection pad to collect all of the ethanol from the perspiration before water vapor from perspiration enters the environmental indicator pad, and the environmental pad to collect all of the environmental ethanol before it can cross the nonocclusive separator layer and enter the collection pad. Thus, because a nonocclusive separator layer separates the two pads in the embodiment as shown in FIG. 6, there is the possibility that some ethanol from one pad may leak into the other pad.

The dermal patch may also be provided with a pouch (not shown) that is preferably a foil-lined vapor-barrier envelope to surround the dermal patch and protective liners (if included). The pouch is useful for storing one or more dermal patches and preventing patch exposure to environmental volatiles before application. A dermal patch may be sterilized in the pouch such as by gamma irradiation and the pouch may include the sterilization date, although the dermal patch itself has no known expiration period. The pouch may be resealable and can be used to store and protect a dermal patch after it has been removed from a wearer and during shipping to an analytical laboratory at ambient temperature (e.g. by surface mail).

Because the preferred polyurethane film of the dermal patch is gas permeable, volatile water and ethanol molecules from the skin can cross the film. When perspiration containing volatile analytes including ethanol crosses the second non-occlusive film into the adsorption pad, the activated carbon adsorbs the vapor phase analytes while the water vapor passes through the adsorptive pad and escapes through the first outer non-occlusive film to the environment. Body heat volatilizes the water in perspiration driving it through the dermal patch. Larger non-volatile molecules (e.g., liquid water) cannot pass through the second inner non-occlusive film and remain trapped against the skin. Liquid water cannot cross the gas permeable film from either the skin or the environment to reach the adsorption pad and vapor phase water in perspiration escapes to the environment, eliminating many disadvantages of an occlusive patch. Moreover, because the dermal patch of the present invention is non-occlusive, equilibrium between the dermal patch and the skin is never reached and the analytes including ethanol accumulate in the adsorption pad during the entire wearing period. At the end of the monitoring period, the dermal patch is removed and the adsorption pad is separated from the dermal patch. The adsorption pad contents are eluted into an aqueous buffer and analyzed.

The dermal patch collects insensible and sensible perspiration from the skin covered by the adsorption pad. Total insensible perspiration from a 1.75 m$^2$ body surface has been measured at 381, 526 and 695 ml/day at 22° C., 27° C. and 30° C., respectively, whereas sensible perspiration varies with an individual's response to thermal, physical or emotional stress (Lamke, L. O., Scand. *J Clin. Lab. Invest.* 37:325, 1977). Insensible perspiration for an individual experiencing minimal thermal, physical and emotional stress is the minimum amount of perspiration that the dermal patch processes during a monitoring period. Thus, using the measurements indicated above, a dermal patch with an adsorption pad of about 14 cm$^2$ processes a minimum of 300 $\mu$l of perspiration per day at 22° C. average temperature. The subject's alcohol consumption during the monitoring period determines the ethanol content in insensible perspiration.

Use of the Patch for Detecting Ethanol Consumption

The dermal patch is applied to and removed from the subject's skin, preferably by a trained technician who chooses a suitable location on the subject's body, avoiding areas of excessive body hair, lesions, abrasions, wounds, scars or dermatological irritations. The dermal patch is preferably attached on either upper arm, the back or lower chest because these skin areas have about the same level of permeability. It will be appreciated that other portions of the body are also appropriate to attaching the dermal patch, such as, for example, the leg, ankle, top or sole of the foot, top or palm of the hand, forearm, neck, upper chest and buttocks, depending on the condition of the skin and other considerations such as privacy concerns. The skin of the selected site is cleaned with an agent to remove surface contaminants (e.g., a standard alcohol wipe containing 70% isopropanol) and the dermal patch is placed on the dry cleaned skin, contacting the adsorption pad and adhesive layer to the subject's skin and then gently pressing the dermal patch to the skin and pressing the adhesive layer gently around the border area of the patch. The adhesive layer becomes translucent with no air bubbles remaining between the adhesive layer and the skin when adhesion is complete. Moreover, complete adhesion produces a subtle puckering of the polyurethane film and the underlying skin, producing a slightly rippled or wavy appearance on the surface of the applied patch. The person applying the dermal patch may also record information such as the application date, the application location, the dermal patch condition and identification number or similar information.

The subject wears the dermal patch for a monitoring period of about 1 hr to several days. Generally, the subject wears the dermal patch for at least 24 hr and up to ten days. The subject is instructed not to rub the dermal patch (e.g., with a towel after washing), but otherwise, no other precautions must be followed while wearing a dermal patch. At the end of the monitoring period, the technician removes the dermal patch.

Before removing the dermal patch, the technician determines visually whether the dermal patch has been compromised during wear by detecting a change in patch appearance generally associated with patch removal or tampering. Because the preferred adhesive layer can be applied securely to a subject's skin only once, removal and reapplication to skin is readily detected by the patch's degree of adhesion and transparency. Exfoliated stratum corneum cells stick to the preferred adhesive during patch removal making secure adhesive reattachment impossible. Moreover, the retained skin cells produce a cloudy nontranslucent appearance to the polyurethane layer with adhesive lower surface at the patch's border. Similarly, rips or punctures to the patch, portions of cloudy appearance in the patch's perimeter border area, discoloration of the patch or surrounding skin, or inflammation around or under the patch are readily detectable evidence of tampering. If removal or tampering is detected, the technician records that information for use in interpreting the analysis results.

During removal, the technician avoids contamination of the adsorption pad by using gloved hands or tweezers to remove the pad and place it into a clean container that is then sealed. The technician removes the patch by gently prying under an edge of the patch to loosen a portion of the adhesive layer from the subject's skin and lifting the patch from the subject's skin to a clean surface where the pad is removed. Alternatively, the dermal patch may be partially removed by loosening a portion of the adhesive and peeling a portion of the patch away from the skin to expose the adsorption pad which remains partially attached to the subject's skin. The adsorption pad is then removed from between the subject's skin and the outer portion of the patch and placed into a clean container as above.

After removal of the dermal patch, the trained person further inspects the removed patch and skin for evidence of prior removal or tampering of the dermal patch. Such evidence includes detection of punctures, rips or tears in the patch or adsorption pad (e.g., detected by holding the patch to a light source), discoloration of the patch or underlying or surrounding skin, and changes in the patch identification number or other indicia. Any changes are recorded and the patch is discarded.

The removed adsorption pad is used for detection of an analyte such as ethanol retained in the activated carbon. Analysis may be done immediately after removing the pad from the dermal patch or the pad can be stored and/or transported to another facility for analysis after the pad has been sealed into a suitable container. Storage and transport of the pad before ethanol analysis may be at ambient temperature and does not require special conditions because ethanol in the adsorption pad is stable at temperatures up to 60° C. for 3 days and at ambient temperature for at least one month.

Once ethanol is adsorbed onto the activated carbon of the adsorption pad, it remains there until it is desorbed by displacing it with another compound such as liquid water, an aqueous solution or an organic solvent that has a higher chemical potential for binding with the carbon. The extracted ethanol can be analyzed by well known methods such as, for example, enzymatic assays, immunoassays, gas chromatography, chemical oxidation and photometry, electrochemical oxidation with fuel cells, infrared spectrometry or solid-state semiconductor sensing.

Although collection and detection of ethanol expressed the skin is the most direct means of detecting ethanol consumption by an individual during the period the dermal patch is worn, the dermal patch of the present invention can also be used to collect and detect a metabolite of ethanol that is expressed through the skin in perspiration, such as acetaldehyde. Acetaldehyde is also adsorbed by activated charcoal in the dermal patch and can be similarly extracted and detected using conventional methods. The level of acetaldehyde produced from consumed alcohol and expressed through the skin is less than that of ethanol expressed through the skin, but is still within detectable levels. Moreover, detection of an ethanol metabolite such as acetaldehyde provides a measure of alcohol consumption even when the individual has been exposed to an amount of environmental ethanol sufficient to negate or interfere with accurate detection of ethanol expressed through the skin in perspiration. That is, a positive detection of acetaldehyde and ethanol in the adsorption material of the dermal patch would suggest alcohol consumption, whereas detection of ethanol without acetaldehyde would suggest environmental exposure to ethanol.

The invention can be better understood by way of the following examples which are representative of the preferred embodiments, but which are not to be construed as limiting the scope of the invention. All of the volunteers who participated in the clinical investigations of the dermal patch provided informed consent. Efficacy of the dermal patch was demonstrated in clinical trials using dermal patches such as illustrated in FIGS. 1–3. These studies included controlled administration of ethanol to volunteers wearing dermal patches and negative control studies of dermal patches worn by non-drinking subjects. Based on these studies, the relationship between a specific ethanol dose and the amount of ethanol collected by a worn dermal patch and detected using conventional methods was determined. These studies show that the dermal patch may be used to monitor human subjects for exposure to ethanol, with sensitivity sufficient to collect, retain and detect ethanol from as little as a single ethanol dose.

EXAMPLE 1

Dermal Patch Application and Removal

A technician wearing sterile gloves cleaned application sites on the subjects' upper arms, back and lower chest with 70% isopropanol alcohol swabs and applied dermal patches as described above. Subjects stretched their skin slightly just before and during dermal patch application by flexing the biceps (for arm application), bending forward (for back application), and bending backward (for lower chest application) to prevent dermal patch from putting tension on the relaxed skin.

The technician examined the dermal patch after it was applied. The peripheral adhesive border area of the patch became uniformly translucent when the patch was properly applied (the adsorption pad remained opaque) and the patch had a slightly rippled or wavy appearance on its surface. The technician replaced the dermal patch if it did not appear to be properly and completely adhered to the subject's skin, e.g., it had raised edges or channels in the adhesive perimeter area where contact was interrupted or incomplete. Close-up photographs of dermal patches were taken just after application and before removal of each dermal patch to assess and record dermal patch integrity; specimen codes, dates and other pertinent information were recorded with the photograph.

After application, the subjects were instructed to wear the patch for a designated time period without disturbing it. Otherwise, subjects performed their normal activities including swimming, manual labor and daily exercise.

After the designated time period, subjects returned to the test facility for patch removal. The technician examined the dermal patch before removal to verify that the dermal patch was securely affixed throughout the wearing period and remained free of holes or tears. That is, the adhesive perimeter portion of the patch retained its translucent appearance with no obvious channels in the adherent film spanning the area between the adsorption pad and the outer perimeter edge of the dermal patch. The technician noted the degree of force needed to remove the dermal patch because a secured dermal patch generally required some effort to remove it from the skin, whereas a partially or completely removed patch was removed with little effort.

The technician wore sterile gloves to remove the dermal patch. As the dermal patch was removed, the adsorption pad was separated from the first and second polyurethane film layers and placed in a clean container which was stoppered and crimp capped. The remaining parts of the dermal patch were removed from the subject and discarded.

After patch removal, the technician further observed and recorded the appearance of the skin that had been under the dermal patch. In a properly adhered patch, the adherent film compressed the skin slightly, forming ridges about 2–3 mm apart that were retained temporarily after patch removal. In contrast, if the adherent film had been removed or disturbed earlier, the skin ridges were absent.

Dermal patches that exhibited any characteristics of removal or nonadherence during the use period or otherwise abnormal appearance or tactile characteristics when removed were noted and retained. The technician appropriately noted anomalous conditions detected during patch removal before sending the pads for analysis, excluding those that had failed to adhere properly. Fewer than 2% of 1,342 dermal patches used in the investigations were excluded because of adherence failure. Only six of 90 patches worn for four to 14 days by subjects who perspired profusely during exercise during the wearing period showed incomplete adherence when the patches were removed. Adsorption pads were stored at −15° C. to about 20° C. during transport to a laboratory for extraction and analysis.

EXAMPLE 2

Adsorption Pad Extraction and Analysis

To avoid potential problems of analyte nonuniformity on the pad, the entire adsorption pad was extracted. Before pad extraction, vials containing the pads were allowed to warm to room temperature. The adsorption pad was removed and placed in a 20 ml glass vial (e.g., a scintillation vial), 2 ml of deionized water was added, the vial was capped and the pad was vortex mixed with the water for 20 seconds. After mixing, the pad and water incubated at room temperature for 4 hr with occasional mixing to form an extract. A 4 hr extraction was considered optimal for speed and aqueous recovery based on results from extractions for 5 min (67% of maximal recovery), 4 hr (88%), and 48 hr (100%); heat or solvent extraction may increase recovery but require additional equipment and reagents. After the 4 hr extraction, 50 $\mu$l of extract was transferred into a labeled conical polypropylene vial, 15 $\mu$l of a 0.005% propionitrile internal standard (Aldrich Chemical Co., Milwaukee, Wis.) was added, and the vial was crimp capped and vortex mixed.

A 1 $\mu$l sample of the mixture was analyzed by gas chromatography (GC) using flame-ionization detection (FID) to detect the presence and amount of ethanol with a Hewlett-Packard (HP) 5790A gas chromatometer with FID, an HP 3390A Integrator, and an HP 7673A Auto Sampler. The GC column (6 ft×⅛ in) was packed with 80/100 Carbopack C with 0.2% Carbowax 1500 (Supelco, Bellefonte, Pa.); the carrier gas was He (30 ml/min), H (45 ml/min) and air (240 ml/min); the oven temperature was 90–100° C. isothermal; the injector temperature was 359° C.; and the detector was 300° C. Under these conditions, the retention times were: methanol, 0.48 min; ethanol, 0.73 min; acetone, 0.97 min; isopropanol 1.19 min, n-propionitrile (internal standard), 1.30 min; and n-propanol, 1.54 min.

A ethanol calibrator (Clinical Standard Solution, College of American Pathologists, Northfield, Ill.), equivalent to 50 nl ethanol/dermal patch, was used as a standard and control samples from pads containing no ethanol or 30, 50, 100 or 200 nl/pad of ethanol were included. Ethanol was quantitated by comparing the ratio of the ethanol peak height to the propionitrile peak height, utilizing the calibration curve for known ethanol concentrations.

EXAMPLE 3

Controlled Single Dose Study

Volunteers received dosages of ethanol in the study and were instructed to avoid contact with ethanol-containing drinks, foods, cosmetics and other substances containing ethanol during the test period. As independent measures of ethanol consumption, breath ethanol was measured using an AlcoSensor III (Intoximeters, Inc., St. Louis, Mo.) and saliva ethanol was measured with the QED A150™ test (STC Diagnostics, Bethlehem Pa.) whenever a dermal patch was removed.

On the day before the ethanol dose, fifteen subjects each received fourteen dermal patches applied as follows: three on left back, two on right back, two on left chest, three on right chest and two on each upper arm.

A single dose of ethanol (contained in 40% Vodka diluted with fruit juice or equivalent) was 1.0 g/kg body weight for male subjects, and 0.85 g/kg body weight for female subjects. Subjects fasted overnight (at least 12 hr) before receiving the ethanol dose and then were given a low fat breakfast (cereal, low fat milk and a banana). The ethanol dose, administered 30 min after the breakfast, was consumed over a 30 min period.

One dermal patch was removed from the left back before the ethanol dose was consumed (pre-dose). Then the dose was administered and the time clock was started after the subject had consumed the dose. At 1, 2.5, and 5.5 hr after the ethanol dose (post-dose), dermal patches were removed from the right chest, left chest, and left back respectively. Dermal patches were removed over the ensuing week as follows: on day 1 (24 hr post-dose), one each from the back, arm and chest; on day 3 (72 hr post-dose), one each from the back, arm and chest; on day 5 (120 hr post-dose) one from the arm; and on day 7 (168 hr post-dose) one each from the back, arm and chest. A total of 300 patches were used: 210 pre-dose and 90 post-dose.

On day 1 post-dose, two fresh dermal patches were applied to the chest and back. These two dermal patches were removed on day 3 and two fresh dermal patches were applied in their place. On day 5 post-dose, the two dermal patches added on day 3 were removed, and replaced with two fresh dermal patches. On day 7, the added dermal patches from day 5 were removed. These six additional dermal patches were used to monitor the subjects' contact with ethanol following the control-administered dose.

Breath alcohol levels were highest at 1 hr post-dose (mean: 0.092%) and dropped by 5.5 hr post-dose (mean: 0.027%) and remained undetectable thereafter. Similarly, saliva alcohol levels were highest at 1 hr post-dose (mean: 0.104%) and dropped by 5.5 hr post-dose (mean: 0.035%) and remained undetectable thereafter.

Mean levels of ethanol collected and detected on the dermal patches were: 3 nl for time 0, about 14.3 nl at 1 hr post-dose; about 27.3 nl at 2 hr post-dose; 56 nl at 5.5 hr post-dose; 52 nl at 24 hr post-dose; 49 nl at 72 hr post-dose; 59 nl at 120 hr post-dose; and 63 nl at 168 hr post-dose. Median levels were 39 nl at 24 hr post-dose; 45 nl at 72 hr post-dose; 68 nl at 120 hr post-dose; and 73 nl at 168 hr post-dose. Three sets of six additional post-dose dermal patches used to monitor the subjects' contact with ethanol following the control-administered dose all had mean and median levels of less than 15 nl/patch suggesting that the subjects avoided ethanol exposure.

These results show that ethanol adsorption by the adsorption pad was delayed relative to breath and saliva ethanol and that the pads retained ethanol as long as seven days after the single dose, whereas the information on ethanol consumption was lost for breath and saliva measurements by one day post-dose.

EXAMPLE 4

Cumulative Low Dose Study

On the day before the ethanol dose was given, eight subjects each received thirteen dermal patches applied as follows: two on the left back, two on the right back, two on the left chest, three on the right chest and two dermal patches on each upper arm (totaling 104 patches). One dermal patch was removed from the right chest before the ethanol dose was administered (pre-dose).

The ethanol dose was equivalent to 0.5 g/kg body weight, contained in a volume of commercially available beer (i.e., 24 oz/55 kg body weight), with no dosage difference dependent on gender. Subjects consumed the beer over a 30 minute period on an empty stomach at the same time of day for seven consecutive days beginning on day 0. The beer was obtained from a single keg, so a consistent alcohol concentration (5.0% by vol) was assured for all subjects over the test period. Breath and salvia ethanol were measured at 30 min post-dose. Dermal patches were removed on days 1, 3, 5 and 7, removing one each from the back, chest, and arm.

Figure 7:
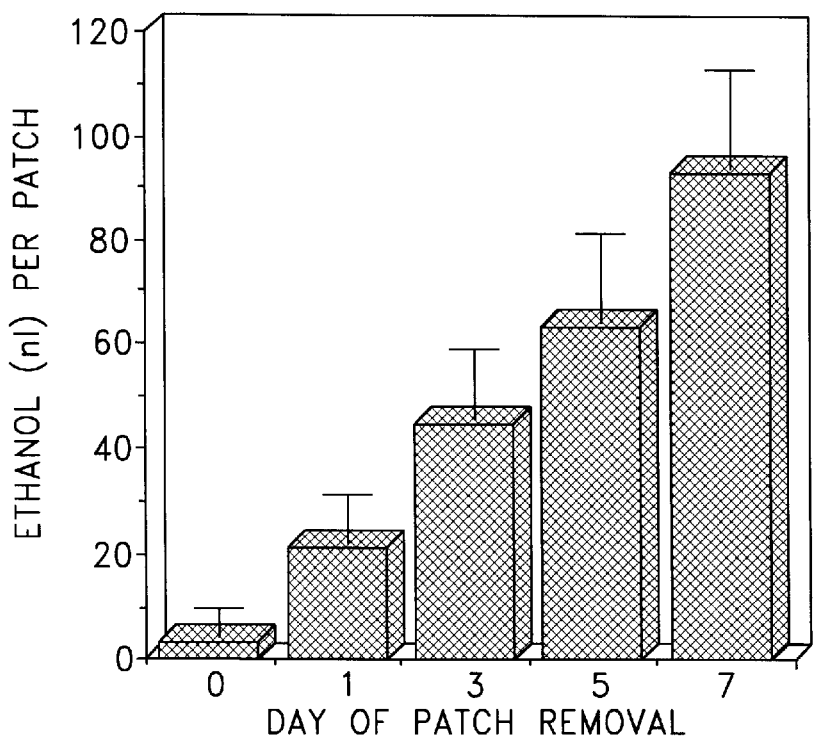
FIG. 7 is a bar graph showing the ethanol content (mean and standard deviation) of patches removed from eight subjects at day 0 (pre-dose) and days 1, 3, 5 and 7 post-dose.

The breath ethanol levels of the eight subjects varied between less than 0.0375% to greater than 0.0525%, with significant variation between individuals and between different test samples for a single individual. As shown in FIG. 7, the mean ethanol content of adsorption pads from patches for the eight individuals increased relatively steadily over time. For example, the mean pad ethanol content at day 3 (three doses totaling 1.5 g/kg) was 45 nl. By day 5 (5 doses totaling 2.5 g/kg), 75% of the pads (18 patches) showed a cumulative ethanol content over 50 nl. These results show that the absorbent pads can accumulate ethanol over time, providing a measurement of the total ethanol consumed over a period of up to seven days.

EXAMPLE 5

Dose Response Study

On the day before ethanol administration, four subjects received six dermal patches (two each on the back, chest and arm); each subject wore a control set of dermal patches for 24 hr pre-dose.

The ethanol dosages were given in increasing amounts equivalent to 0.17, 0.33, 0.5, 0.67, 0.83 and 1.0 g/kg body weight, administered as in Example 3, with doses given 24 hr apart for the first three, and 48 hr apart for the last three. Breath and saliva ethanol measurements were taken at 30 min post-dose. At 24 hr after each dose, but before the next dose, the six dermal patches were removed, and replaced by six fresh dermal patches. Thus, for each dose, six dermal patches were applied and a total of 168 pads were analyzed.

Figure 8:
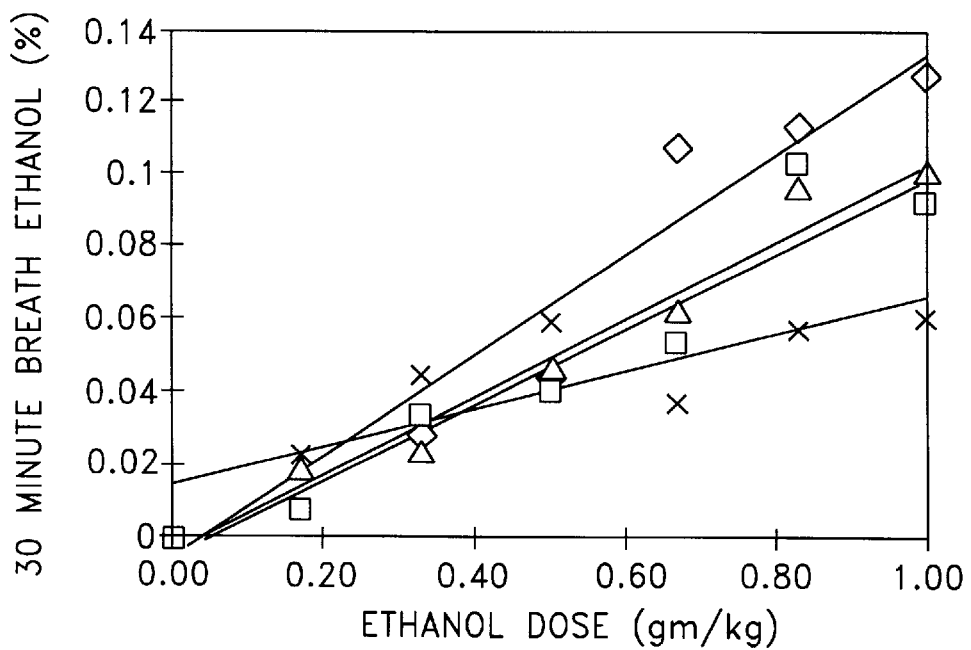
FIG. 8 graphically shows the relationship of breath ethanol measurements to the ethanol dose measured 30 min post-dose for each of the four subjects (subject A: ♦; subject B: ■; subject E: ▲; and subject G: x).
Figure 9:
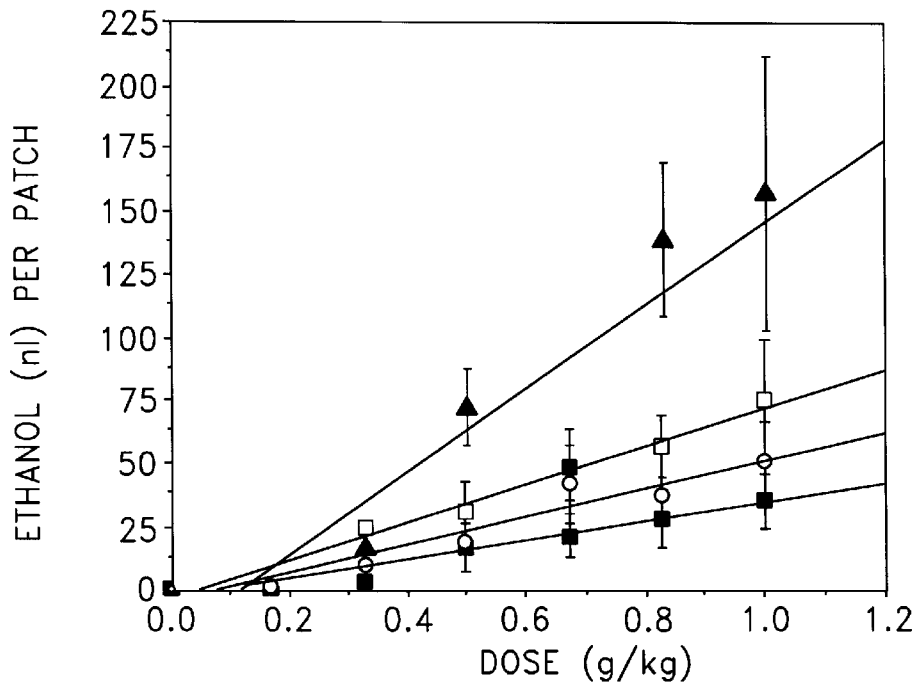
FIG. 9 graphically shows the relationship of ethanol content from dermal patches (mean and standard deviation of six patches for each of seven ethanol doses) relative to the ethanol dose for each of the four subjects (subject A: □; subject B: ▲; subject E: ■; and subject G: ○).

FIG. 8 shows the relationship of breath ethanol measurements to the ethanol dose for each of the four subjects. The data points show significant variation between the breath ethanol detected and the dose administered, with correlation coefficients ($R^2$) for the data points and the lines varying from 0.69 to 0.97 (0.94, 0.92, 0.97 and 0.69 for subjects A, B, E and G, respectively). Similar results were obtained for the saliva ethanol tests (data not shown). FIG. 9 shows a similar plot for the ethanol content (mean of six patches, two each from the arm, back and chest for each subject) of the absorbent pads for the same four subjects compared to the ethanol dose, with correlation coefficients ($R^2$) varying from 0.87 to 0.97 (0.97, 0.87, 0.95 and 0.93 for the data points and lines for subjects A, B, E and G, respectively). The results of this study show the difficulty of quantitating ethanol consumption based on breath ethanol, saliva ethanol or ethanol adsorbed by a dermal patch.

EXAMPLE 6

Negative Control Study

Twenty-one subjects participated. Eighteen wore eight dermal patches for seven days, applied as follows: four on the arms, two on the back, and two on the chest. The other three subjects wore four patches on the upper arms for 3 days. No ethanol was administered and subjects were asked to abstain from alcohol consumption for 24 hr before dermal patch application and while the dermal patches were worn, and to avoid using products containing ethanol or SD alcohol during that time. Breath and saliva ethanol measurements were taken on day 0 as the dermal patches were applied and when the dermal patches were removed (day 3 or day 7). Absorbent pads were assayed for ethanol content using GC with FID as described above.

Of 146 patches analyzed (10 were compromised during wearing and not analyzed), the mean alcohol content was 26±12 nl, and only four patches had over 50 nl. These results probably reflect accumulation over a week of endogenous ethanol normally produced in the body and inadvertent exposure to ethanol in cosmetics or household chemicals. When the median ethanol content measurements were compared for the different body locations of the patches, they were indistinguishable (at a 95% confidence level; p<0.05). While there was some variation between patches obtained from an individual subject, most subjects' patches showed similar ethanol levels independent of the patch location.

EXAMPLE 7

Dermal Patch Placement Study

Three subjects each received eighteen dermal patches applied on day 0 as follows: three each on the right and left arms, right and left back, and right and left chest (54 total). Subjects were given a single 1.0 g/kg ethanol dose as in Example 3 and patches were removed on day 3 post-dose and absorbent pads analyzed to ethanol content by GC as described above. Breath and saliva ethanol measurements were taken pre-dose, 30 minutes post-dose, and at day 3 during dermal patch removal.

The ethanol content (mean and median) of the pads from the six different locations did not differ (at a 95% confidence level; p<0.05), although for a single location the largest range was seen for the right arm and the smallest range variation was seen for the left back. Moreover, there was a high correlation ($\geq 0.84$, generally $\geq 0.90$) between the ethanol dose detected and all of the patch locations. Thus, all of the application locations are equivalent for collecting and retaining ethanol in the patch.

EXAMPLE 8

Kinetic Study: Sequential Accumulation Over a 48 hr Period

On the day before ethanol dosing, four subjects each received three dermal patches applied as follows: one each to the chest, back and arm. During this study, subjects received additional sets of patches just before the dose (time 0) and at 1, 2, 4, 8, 12, 24, 48 and 72 hr post-dose (a total of 27 patches per subject and 108 for the study). Dosing was as described in Example 3. Before the ethanol dose was administered, the three dermal patches were removed, breath and saliva ethanol levels were measured, and three fresh dermal patches were applied in the same locations. At 1 hr post-dose, breath and saliva measurements were made, dermal patches were removed and fresh dermal patches were applied. This procedure was repeated at 2, 4, 8, 12, 24, and 48 hr post-dose. The ethanol collected on the dermal patches in this phase represents the ethanol accumulation over the interval of dermal patch wear.

The mean breath and saliva ethanol levels were 0.094% and 0.103%, respectively, a 1 hr post-dose. At 2 hr post-dose, the mean breath ethanol decreased to 0.090% and the mean saliva ethanol level increased to 0.119%, but by 4 hr post-dose both breath and saliva ethanol levels were about half of their highest values and were undetectable by 8 hr post-dose. Ethanol detected in the adsorption pads measured (mean values): 8 nl at 1 hr post-dose, 10 nl at 2 hr post-dose, 23 nl at 4 hr post-dose, 22 nl at 8 hr post-dose, and undetectable thereafter. After 8 hr post-dose, no ethanol above baseline was detected in the absorbent pads. Thus, the dermal patch can be used detect ethanol in approximately the same time range as detected by breath and saliva testing (1 to 4 hr post-dose), but can also be used detect ethanol between 4 hr and 8 hr post-dose, when no ethanol was detected by breath and saliva testing. Although there is some delay in detection of ethanol in perspiration compared to breath and saliva testing, ethanol can be collected from perspiration up to 48 hr post-dose, when breath and saliva would no longer be detectable, and the patch of the present invention can retain the perspiration ethanol for up to 8 days post-dose providing a much longer period for detection of ethanol consumption that possible with breath and saliva testing.

Figure 10:
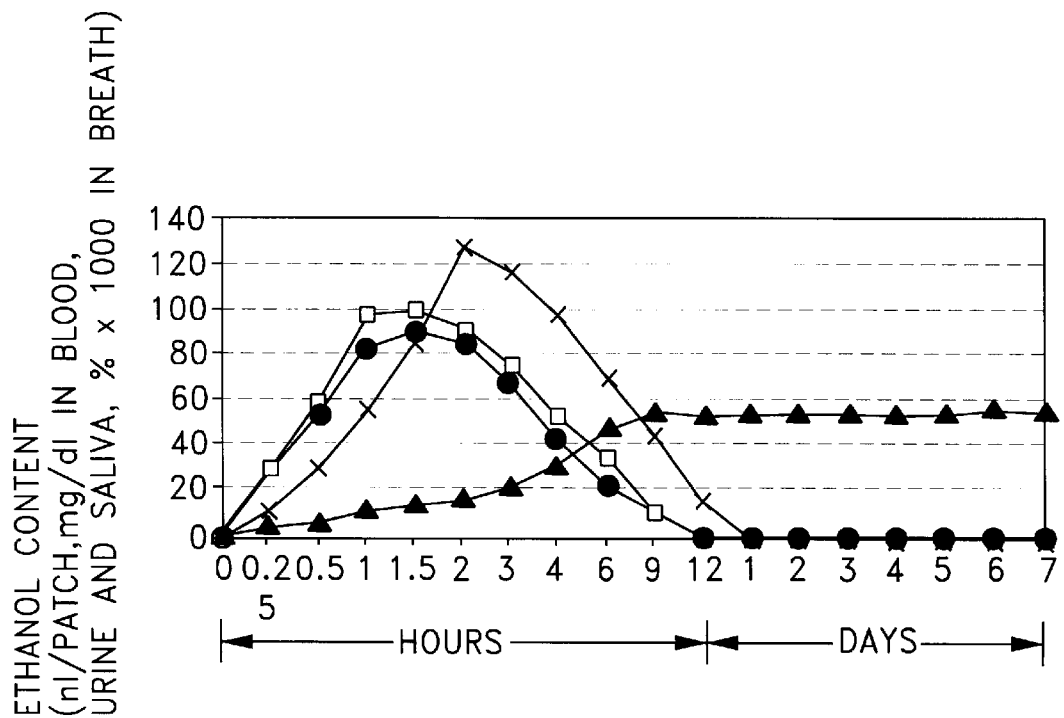
FIG. 10 graphically shows a typical kinetic relationship of ethanol measured in blood saliva (□, solid line), breath (●, solid line), urine (x, shaded line), and collected from perspiration using the dermal patch (▲, shaded line) for one subject.

FIG. 10 shows a typical kinetic relationship of ethanol in blood, urine, saliva and collected from perspiration using the dermal patch. The Y-axis presents the ethanol content of the dermal patch (nl); blood, saliva and urine (mg/dl) and breath (%) for a subject who received 1 g/kg of ethanol at time 0. The blood ethanol was measured up to 5.5 hr post-dose and interpolated from there based on published ethanol metabolism rates (Jones A. W. et al., *Clin. Chem.* 38(5):743, 1992; Sidell, F. R. & Press, J. E., *Psychopharmacol.* 19:246, 1971); urine content was based on the blood ethanol levels and the published relationship between blood and urine ethanol levels (Biasotti, A. A. & Valentine, T. E., *J. For. Sci.* 30(1):194, 1985). FIG. 10 shows that blood, saliva and breath ethanol levels rise more quickly relative to that collected in the dermal patch and then drop after about 2 hr post-dose, returning to baseline by 24 hr post-dose. In contrast, ethanol collected in the dermal patch is cumulative, peaking at about 9 to 12 hr post-dose, and retained until the patch is removed.

Based on the clinical studies, the best ethanol concentration for the GC cutoff calibrator, the sensitivity and specificity of GC for possible cutoffs (10, 20, 30, 35, 40, 50, 60 and 70 nl/pad) were calculated by analysis of the number of true positives, false positives, false negatives and true negatives for 791 patches from 35 subjects. The optimum cutoff concentration, 30 nl/pad, resulted in the fewest false positives and false negatives, thus giving the highest sensitivity and specificity for the assay.

The limit of quantitation (LOQ) is the lowest concentration of ethanol that can be reliably quantitated by GC for known ethanol concentrations in dermal patch extracts. The LOQ was 16 nl/patch based on seven of ten assays in which more than 50% of the samples were within ±50% of the known concentration of ethanol concentration for the sample.

Clinical and diagnostic sensitivity and specificity were determined using standard procedures ("Proposed Guideline: Assessment of clinical sensitivity and specificity of laboratory tests" *NCCLS Document GP*-10, Vol. 7, No. 6, 1987; Galen, R. S. & Gambino, S. R., "Beyond Normality: The predictive value and efficiency of medical diagnoses," Wiley Biomedical Publications, 1975 (John Wiley & Son, New York, N.Y.); and Spiehler, V. R. et al., *Clin. Chem.* 33:1535, 1988). Using a GC cutoff of 30 nl/patch, the diagnostic sensitivity was 90.38% (determined from 364 dermal patch results after 24 hr minimal wear from subjects administered known ethanol doses) and the diagnostic specificity of 85.95% (determined from 427 dermal patch results from subjects who received no ethanol dose and said they had not consumed alcohol during the wear period). The clinical sensitivity and specificity were determined from dermal patch results obtained for subjects in controlled studies given known doses (0.85 g/kg for females and 1.0 g/kg for males), producing a positive predictive value for ethanol consumption of 86.5% and a negative predictive value for abstinence from ethanol of 90.9%.

EXAMPLE 9

Dermal Patch Analysis After Immersion in Liquids

Immersion studies were used to determine whether ethanol would leave the dermal patch during wear if the dermal patch were soaked in water at relatively high temperatures (40±1° C. in liquid). Blank dermal patches were spiked with about 100 nl of ethanol and then attached to petri dishes to simulate a dermal patch attached to skin. A control set of three patches was stored dry at 40±1° C. and the test sets of three patches each were immersed in a water bath at 40±1° C. containing ordinary tap water with or without 5 PPM chlorine, 0.9% NaCl (common salt water) or 0.18% bubble bath soap. For comparison, swimming pool water containing 3 PPM chlorine has a strong chlorine smell and irritates eyes; and 0.18% bubble bath soap is equivalent to adding an 8 ounce bottle of bubble bath soap to a forty gallon bathtub of water. At the end of 3 hr and 24 hr, the control patches and test patches were dismantled and the adsorption pad recovered and assayed for ethanol using the standard procedures essentially as described above. The results of these tests, shown in Table 1, show that ethanol in the patches was recoverable even after exposure to high temperatures.

TABLE 1

Mean and standard deviation of recovered ethanol (nl/patch)

| Conditions | 3 hr Exposure | 24 hr Exposure |
| --- | --- | --- |
| Control (dry) | 109 ± 15 | 104 ± 10 |
| Tap water | 101 ± 14 | 105 ± 22 |
| 5 PPM Chlorine solution | 107 ± 12 | 108 ± 6 |
| NaCl solution | 116 ± 3 | 103 ± 24 |
| Soap solution | 123 ± 13 | 147 ± 7 |

Immersion in water, chlorine solution and salt solution did not significantly affect the detectable ethanol in the pads showing that the outer polyurethane layer of the dermal patch effectively isolates the adsorption pad from the environment. Immersion for hours in bubble bath soap solution increased the ethanol concentration probably because the bubble bath soap used contained ethanol (2146 mg %) which was adsorbed across the outer polyurethane film. Avoidance of ethanol-containing household products during dermal patch use would prevent such uptake of ethanol from the environment. Alternatively, a dermal patch with two adsorption pads as illustrated in FIGS. 4–6 and discussed above may be used to monitor environmental ethanol exposure and serve as an internal control (baseline) for the perspiration collection pad.

EXAMPLE 10

Microorganism Studies

These studies were conducted to (1) confirm that the adsorption pad encased in the first and second polyurethane layers of a sterilized dermal patch remains sterile during seven days of dermal patch wear; (2) identify and quantitate the specific microorganisms recovered from underneath the dermal patch worn for seven days; and (3) evaluate the effects of the identified microorganisms on ethanol contained on the adsorption pad. The ability of an identified microorganism to produce or metabolize ethanol in a dermal patch environment was based on known biosynthetic and catabolic characteristics of the identified microorganisms.

Standard arm skin swabs from eight subjects were taken in the approximate location and area size where the adsorption pad would contact the skin. Using a template to limit the area, a swab specimen of the skin was collected. The same location on the arm was then prepared for dermal patch wear by following the standard isopropanol skin prep protocol as described above. After the isopropanol evaporated, a second skin swab specimen was taken from the treated area, again using the template. Two standard alcohol dermal patches were then applied, one directly over the prepared swab zone, and the second next to it. The patches were worn for seven days during which the subjects were instructed to avoid contact with ethanol.

At the end of the seven days, the first dermal patch was removed, and the skin under the adsorption pad was swabbed as described above. The second dermal patch was removed, and the adsorption pads were isolated using aseptic procedures. Swab samples from the day of dermal patch application, from the day of patch removal, and the worn adsorption pads were extracted with growth media and the extract was cultured on nutritional agar plates (3 days, 37° C.) to promote growth of aerobic microorganisms using standard microbiology procedures. The types and numbers of colony forming units (CFU) of microorganisms (staphylococci, micrococci, diphtheroids and bacilli) were determined using standard microbiological techniques.

The pads generally remained sterile during the test period. No fungi or other yeast (i.e., <5 CFU/sample) were detected in any sample. Only one of the eight subjects had consistently high CFU on the skin and under the dermal patch ($25-40 \times 10^3$ CFU/sample, identified as Staphylococcus epidermis). Other samples showed a mixture of significantly lower numbers (about $<10^2$ CFU/sample) of gram positive cocci and rods, consistent with the types of normal microbial flora associated with skin. The isopropanol disinfection reduced the number of CFU recovered about 10-fold lower. Based on the types and numbers of microorganisms recovered from patches applied to the isopropanol disinfected areas, it is extremely unlikely that organisms recovered from the skin under the patch or the pad itself would affect the alcohol concentration detected from an adsorption pad recovered from a dermal patch.

These results show that the nonocclusive patch does not increase bacterial growth or affect the microflora type during the wearing period. That is, for skin that was not isopropanol disinfected before patch application, the number and type of microorganisms was approximately the same as samples taken from uncovered skin. For skin that was isopropanol disinfected before patch application, the number of microorganisms was decreased relative to samples taken from uncovered skin and the type of flora detected did not change significantly.

In contrast, occlusive patches are known to increase bacterial growth about 100-fold to 10,000-fold compared to exposed skin when worn for three to five days (Aly Raza et al., *J. Invest. Dermatol.* 71(6):378–381, 1978; Aly, Raza et al., *Am. J Infect. Control* 16(3): 95–100, 1988).

EXAMPLE 11

Comparative Quantitative Assessment of Skin Under Nonocclusive and Occlusive Patches Changes in skin under a nonocclusive patch as described herein are compared to changes to skin under an occlusive patch having the same dimensions as the nonocclusive patch but made of three layers of vinylidene polymer plastic film. Specifically, the changes assessed include: pH at the skin surface, transepidermal water loss ("TEWL"), and $CO_2$ emission rates. All measurements are begun immediately after the dermal patch is removed from the skin. The skin pH is measured using a calibrated pH meter with a flat surface electrode using standard procedures. After the dermal patch is removed at the time described below, the electrode is dipped in a pH 7 phosphate buffer, applied to the skin formerly covered by the patch and held in place until the pH reading stabilizes. Two to four measurements per dermal patch are taken at the time intervals described below and the arithmetic mean of the measurements is recorded. TEWL is measured with an electrolytic water analyzer as previously described (Aly Raza et. al., *J. Invest. Dermatol.* 71(6):378–381, 1978). Briefly, a 0.64 cm$^2$ cup is placed on the skin and high purity $N_2$ gas is passed at 100 cc/min from a molecular sieve to remove residual water into the measuring cup and the effluent is directed into a water analyzer. Measurements are taken 20 minutes after cup placement on the skin to remove water from perspiration trapped under the dermal patch. The $CO_2$ emission rate is measured using an infrared analyzer as previously described by Aly (id.). Briefly, a 9.6 cm$^2$ cup is applied to the skin and high purity $N_2$ gas is passed at 50 cc/min through the cup to collect $CO_2$ emissions which are measured by the analyzer at 20 min after the cup is placed on the skin.

Six dermal patches are applied to both arms of five volunteers (using the standard isopropanol skin prep protocol as described above): three occlusive patches per arm and three nonocclusive patches per arm. The patches are worn for up to seven days during the testing period, with one arm used to take measurements periodically during the testing period and one arm used to take a single measurement at the seventh day (i.e., the set of patches are worn for the entire seven days without interim removal of patches). For the periodically tested skin areas the following protocol is used. After about 24 hr, one of each type of patch is removed for measuring each of the three parameters (pH, TEWL and $CO_2$ emission, one measurement per patch-covered area) from one arm and measurements are taken and recorded for a "day 1" measurement. After the measurements are taken, the same types of patches are reapplied to the same areas from which the "day 1" measurements are taken and the second set of patches remains in place for an additional two days. Then, the patches are removed and "day 3" measurements are taken for each of the patches as described above. After the measurements are completed, the patches are again replaced as described above and after an additional two days, the patches are removed and "day 5" measurements are made as described above. After the measurements are completed, the patches are again replaced and worn for an additional two days when "day 7" measurements are taken as described above. Day 7 measurements are also made for the areas of skin under that patches that were worn without removal for the complete seven day period. As controls, skin that was not under any patch was also measured for each of the three parameters at each measuring day (days 1, 3, 5 and 7).

The pH of uncovered skin is moderately acidic (3.8 to 4.5) for each of the measurement times. The pH of skin under the nonocclusive patch does not differ significantly from that of the uncovered skin for any time during the seven day period and skin under the removed-and-replaced patch does not differ significantly from the skin under the continuous-wear patch. The pH of the skin under the occlusive patch increases to a relatively neutral pH over the testing period. The pH is about 4.5 at day 1, about 6.5 at day 3, about 6.8 at day 5. and about 7.0 at day 7. The skin under the occlusive patch worn for the entire seven days without removal does not differ significantly from that under the occlusive patch that is removed and replaced during the seven day period.

The TEWL measurements are about 0.5 to 0.6 mg/cm$^2$/hr for uncovered skin at all measurement times. The TEWL measurements for the skin under the nonocclusive patches does not differ significantly from those for the uncovered skin during the testing period and does not differ significantly whether the patch is removed and replaced or remains in place for the full seven days. The TEWL measurements for the skin under the occlusive patches increased significantly from those for the uncovered skin during the testing period. By day 1, TEWL is about 1.2 mg/cm$^2$/hr, at day 3 is about 1.6 mg/cm$^2$/hr, at day 5 is about 1.8 mg/cm$^2$/hr and at day 7 (for both day 7 patches) is about 2.0 mg/cm$^2$/hr.

The $CO_2$ emission rate is about 25 nl/cm$^2$/min for uncovered skin throughout the testing period. For the skin under the nonocclusive patches, the $CO_2$ emission rate does not differ significantly from that of the uncovered skin during the testing period and does not differ significantly whether the patch is removed and replaced or remains in place during the entire testing period. In contrast, the $CO_2$ emission rate for skin under the occlusive patch increases during the testing period. On day 1, the rate is about 80 nl/cm$^2$/min; on day 3, is about 105 nl/cm$^2$/min; on day 5, is about 120 nl/cm$^2$/min; and on day 7 (for both day 7 measurements) is about 125 nl/cm$^2$/min.

These results, taken together, show that there are significant and quantitative differences between the nonocclusive patch of the present invention and an occlusive patch of the same dimensions. These differences significantly contribute to the comfort level of the wearer, allowing the wearer to comfortably wear the nonocclusive patch during the longer periods that are desirable for collecting and monitoring alcohol usage.

The dermal patch and method of the present invention are useful for collecting and detecting volatile analytes including ethanol in perspiration, and can serve as an alternative or adjunct to urine specimen collection and analysis. The dermal patch is useful for monitoring a subject's ethanol use during an extended time period during which the patch is worn. Thus, it is useful for determining abstinence from ethanol use over time in people such as alcoholics, parolees, persons receiving particular medical treatments or who perform safety-related jobs such as machinery or vehicular operation. The dermal patch and method of analysis for alcohol consumption are also useful for discovery of new therapeutic drugs or treatments to preclude or limit alcohol consumption by individuals who should avoid alcohol consumption. The invention is useful for monitoring people being treated with drugs or therapy designed to make alcohol unpalatable to the treated subject to determine if treatment results in alcohol avoidance.

Unless defined otherwise, all scientific and technical terms used herein have the same meaning as commonly understood by those skilled in the relevant art. Unless mentioned otherwise, the techniques employed or contemplated herein are standard methodologies well known to one of ordinary skill in the art. The examples of embodiments are for illustration only.

Although the present invention has been described in the context of particular examples and preferred embodiments, it will be understood that the invention is not limited to such embodiments. Instead, the scope of the present invention shall be measured by the claims that follow.

What is claimed is:

1. A dermal patch for determining the presence of an analyte in perspiration of a subject mammal, comprising:
    an adsorbent material for collecting perspiration in vapor phase from a subject's skin and retaining a vapor phase analyte present in said collected vapor phase perspiration, said adsorbent material having a first side and a second side and an outer perimeter, wherein said first side is adapted to be in fluid communication with the subject's skin;
    a first gas permeable film having a first side and a second side and an outer perimeter, wherein said first side of the gas permeable film is adjacent to said second side of said adsorbent material and wherein said first gas permeable film has a first moisture vapor transmission rate (MVTR) whereby perspiration expressed through the subject's skin is permitted to escape in vapor phase from said patch through said first gas permeable film; and
    a second gas permeable film having a first side and a second side and an outer perimeter, wherein said first side of the second gas permeable film is adapted to be in fluid communication with the subject's skin and said second side of the second gas permeable film is located adjacent to said first side of said adsorbent material, and wherein said second gas permeable film has a second MVTR that is no more than about equal to said first MVTR.

2. The dermal patch of claim 1, further comprising an adhesive layer on said first side of said first gas permeable film, said adhesive layer for attaching said patch to the subject's skin.

3. The dermal patch of claim 1, further comprising an adhesive layer on said first side of said second gas permeable film, said adhesive layer for attaching said patch to the subject's skin.

4. The dermal patch of claim 1, further comprising a release liner having a first side and a second side, wherein said release liner is located between said first gas permeable film and said adsorbent material such that said first side of said release liner is adjacent to said first side of said first gas permeable film and said second side of said release liner is adjacent to said second side of said adsorbent material.

5. The dermal patch of claim 1, further comprising an outer protective liner located proximate to said second side of said first gas permeable film, to said first side of said second gas permeable film, or both.

6. The dermal patch of claim 1, wherein said adsorbent material comprises activated carbon in an inert matrix.

7. The dermal patch of claim 1, wherein the analyte retained in said adsorbent material comprises ethanol.

8. The dermal patch of claim 1, wherein said first or second gas permeable film comprises polyurethane.

9. The dermal patch of claim 1, further comprising a pouch for containing the dermal patch before use, after use or both.

10. The dermal patch of claim 1, further comprising indicia incorporated into the dermal patch for identifying the dermal patch.

11. A dermal patch to be worn on the skin of a subject mammal for determining the presence of ethanol in the subject's perspiration, comprising:
    a carbon-containing adsorption pad for collecting vapor phase perspiration from a subject's skin and retaining vapor phase ethanol present in said collected perspiration, said adsorption pad having a first side and a second side, wherein said first side is adapted to be in fluid communication with the subject's skin;
    a first gas permeable film having a first side and a second side and an outer perimeter, wherein said first side of the gas permeable film is located adjacent to said second side of said carbon-containing adsorption pad, and wherein said first gas permeable film has a first moisture vapor transmission rate (MVTR); and a second gas permeable film having a first side and a second side and an outer perimeter, wherein said first side of the second gas permeable film is adapted to be in fluid communication with the subject's skin and said second side of the second gas permeable film is located adjacent to said first side of said adsorption pad, and wherein said second gas permeable film has a second MVTR that is no more than about equal to said first MVTR.

12. The dermal patch of claim 11, further comprising an adhesive layer on said first side of said gas permeable film, said adhesive layer for attaching said patch to the subject's skin.

13. The dermal patch of claim 11, further comprising an adhesive layer on said first side of said second gas permeable film, said adhesive layer for attaching said patch to the subject's skin.

14. The dermal patch of claim 11, wherein said first or second gas permeable film comprises polyurethane.

15. The dermal patch of claim 11, wherein said first and second gas permeable films comprise polyurethane.

16. The dermal patch of claim 11, further comprising a release liner having a first side and a second side, wherein said release liner is located between said first gas permeable film and said adsorption pad such that said first side of said release liner is adjacent to said first side of said first gas permeable film and said second side of said release liner is adjacent to said second side of said adsorption pad.

17. The dermal patch of claim 11, wherein said adsorption pad comprises activated charcoal in an inert matrix.

18. The dermal patch of claim I 1, further comprising a pouch for containing the dermal patch before use, after use or both.

19. The dermal patch of claim I 1, further comprising indicia for identifying the dermal patch.

20. A dermal patch for determining the presence of an analyte in perspiration of a subject mammal, comprising:

a first adsorption pad for collecting perspiration in vapor phase from a subject's skin and retaining a vapor phase analyte present in said vapor phase perspiration, said adsorption pad having a first side and a second side and an outer perimeter, wherein said first side is adapted to be in fluid communication with the subject's skin;

a second adsorption pad for collecting said vapor phase analyte from a subject's environment and retaining said analyte, said second adsorption pad having a first side and a second side and an outer perimeter, wherein said second side is adapted to be in fluid communication with the subject's environment;

a first gas permeable film having a first side and a second side and an outer perimeter, wherein said first side of the first gas permeable film is adjacent to a second side of at least one adsorption pad, wherein said second side of said first gas permeable film is adapted to be in fluid communication with the subject's environment, and wherein perspiration expressed through the subject's skin is permitted to escape in vapor phase from said patch through said first gas permeable film;

a second gas permeable film having a first and second side and an outer perimeter, wherein said first side of the second gas permeable film is adapted to be in fluid communication with the subject's skin, wherein said second side of the second gas permeable film is located adjacent to a first side of at least one adsorption pad, and wherein said first side of said second gas permeable film is adapted to be in fluid communication with the subject's skin; and a separator layer located between said first adsorption pad and said second adsorption pad.

21. The dermal patch of claim 20, wherein said separator layer has a first side and a second side, and wherein said first side of said separator layer is located proximate to said second side of said first adsorption pad and said second side of said separator layer is located proximate to said first side of said second adsorption pad.

22. The dermal patch of claim 20, wherein said first adsorption pad is located proximate to said second adsorption pad in a side-by-side arrangement such that a portion of the perimeter of said first adsorption pad is proximate to a portion of the perimeter of said second adsorption pad and said separator layer is located adjacent to the perimeter and the first side of said second adsorption pad, thereby separating the proximate portions of the perimeters of said first and second adsorption pads and separating said second adsorption pad from said second gas permeable film.

23. The dermal patch of claim 20, further comprising an outer protective liner located adjacent to the first side of said second gas permeable film.

24. The dermal patch of claim 20, further comprising an outer protective liner located adjacent to the second side of said first gas permeable film.

25. The dermal patch of claim 20, wherein said analyte comprises ethanol.

26. The dermal patch of claim 20, further comprising a pouch for containing the dermal patch before use, after use or both.

27. The dermal patch of claim 20, further comprising indicia incorporated into the dermal patch for identifying the dermal patch.

28. A method of determining the presence of an analyte contained in the perspiration of a subject mammal, comprising the steps of:

removably attaching a dermal patch to a subject's skin, wherein said dermal patch comprises a carbon-containing material capable of adsorbing a vapor phase analyte contained in the subject's perspiration, a first gas permeable film and a second gas permeable film, wherein said carbon-containing material is located between said first and second gas permeable films and is adapted to be in fluid communication with the subject's skin when said dermal patch is placed on the subject's skin, and wherein said first gas permeable film has first and second sides and wherein the second side of the first gas permeable skin faces away from the subject's skin when the dermal patch is attached to the subject's skin and; wherein said first gas permeable film permits vapor phase perspiration to escape from said dermal patch;

passing vapor phase perspiration containing said analyte expressed from the subject's skin through said carbon-containing material for a period of time sufficient to adsorb said analyte;

removing said dermal patch after a period of time sufficient to adsorb said analyte has elapsed; and determining the amount of analyte adsorbed in said carbon-containing material.

29. The method of claim 28, wherein the removing step occurs about one hour to about ten days after the attaching step.

30. The method of claim 28, wherein the determining step includes extracting said analyte from said carbon-containing material to produce an extract.

31. The method of claim 30, wherein said analyte comprises ethanol which is extracted from said carbon-containing material with water.

32. The method of claim 30, further including a step of measuring said analyte in said extract by gas chromatography.

33. The method of claim 28, further including a step of examining the dermal patch for evidence of tampering or of partial or complete removal of the dermal patch before the removing step.

34. The method of claim 28, wherein the attaching step includes attaching a dermal patch to skin on the subject's arm, the back, the chest or any combination thereof.

35. The method of claim 28, wherein said analyte comprises ethanol.

36. The method of claim 28, wherein said dermal patch further includes a second carbon-containing material that is adapted to be in fluid communication with said vapor phase analyte in the subject's skin, and the method further includes the steps of:

collecting said vapor phase analyte in the subject's skin during the period when vapor phase perspiration containing said analyte is passed through said carbon-containing material; and determining the amount of said analyte adsorbed in said second carbon-containing material.

37. The method of claim 36, further including the step of comparing the amount of analyte in the second carbon-containing material with the amount of analyte in said carbon-containing material through which vapor phase perspiration passed to determine an amount of said analyte in the subject's perspiration during the period when vapor phase perspiration containing said analyte passed through said carbon-containing material.

38. A method of indicating alcohol consumption by a patient, comprising the steps of:

identifying a patient to be monitored for alcohol consumption;

providing a non-occlusive dermal patch having an activated charcoal layer therein;

securing the dermal patch to the skin of the patient for a period in excess of about one day;

permitting moisture in perspiration to escape from the patient and through the dermal patch during said period;

removing the dermal patch from the skin of the patient; and measuring ethanol or a metabolite of ethanol contained in the activated charcoal layer.

39. The method of claim 38, wherein the period is up to about ten days.

40. The method of claim 38, wherein the metabolite of ethanol comprises acetaldehyde.

* * * * *